United States Patent
Murakami et al.

(10) Patent No.: US 8,235,578 B2
(45) Date of Patent: Aug. 7, 2012

(54) AGITATION VESSEL

(75) Inventors: Miyuki Murakami, Tokyo (JP);
Nobuyoshi Tsuda, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 1030 days.

(21) Appl. No.: 11/663,383

(22) PCT Filed: Sep. 16, 2005

(86) PCT No.: PCT/JP2005/017193
§ 371 (c)(1),
(2), (4) Date: Apr. 9, 2007

(87) PCT Pub. No.: WO2006/033307
PCT Pub. Date: Mar. 30, 2006

(65) Prior Publication Data
US 2008/0074945 A1 Mar. 27, 2008

(30) Foreign Application Priority Data
Sep. 22, 2004 (JP) .................................. 2004-275230

(51) Int. Cl.
*B01F 11/02* (2006.01)
*B06B 1/00* (2006.01)
(52) U.S. Cl. ........ 366/115; 366/127; 366/143; 422/127; 422/224
(58) Field of Classification Search .......... 366/108–129, 366/143; 422/100, 224–231, 68.1–82.11, 422/127, 128
See application file for complete search history.

(56) References Cited

U.S. PATENT DOCUMENTS

| | | | |
|---|---|---|---|
| 3,198,489 A * | 8/1965 | Finch ............................. | 366/113 |
| 3,680,841 A * | 8/1972 | Yagi et al. ...................... | 366/118 |
| 4,704,774 A * | 11/1987 | Fujii et al. ..................... | 29/25.35 |
| 4,869,768 A * | 9/1989 | Zola .............................. | 156/245 |
| 4,939,826 A * | 7/1990 | Shoup .......................... | 29/25.35 |
| 5,042,493 A * | 8/1991 | Saito et al. ..................... | 600/459 |
| 5,125,410 A * | 6/1992 | Misono et al. ................. | 600/463 |

(Continued)

FOREIGN PATENT DOCUMENTS
DE       103 25 307    *   7/2004

(Continued)

OTHER PUBLICATIONS

Specification of U.S. Appl. No. 60/513,857, filed Oct. 24, 2003 which matured to U.S. patent 7,808,642, total 12 pages.*

*Primary Examiner* — Tony G Soohoo
(74) *Attorney, Agent, or Firm* — Kilpatrick Townsend & Stockton LLP

(57) ABSTRACT

Provided here is an agitation vessel which enhances energy transmission efficiency in an agitation apparatus and an analysis apparatus, simplifies the structure of the agitation apparatus and the analysis apparatus, and allows for downsizing and improved maintenanceability. An agitation vessel (5) agitates retained liquid by sound waves. A sound wave generating member (24) which generates sound waves is provided integrally with the agitation vessel (5). The agitation vessel (5) includes a bottom wall (5d) and plural side walls (5c) made of an optically transparent material, and a part of the opposing side walls among the plural side walls (5c) is a photometric window (5b) that optically measures the liquid agitated. The sound wave generating member (24) is arranged on the side wall (5c), on which the photometric window (5b) is arranged, among the plural side walls (5c).

14 Claims, 21 Drawing Sheets

U.S. PATENT DOCUMENTS

| | | | | |
|---|---|---|---|---|
| 5,402,791 A * | 4/1995 | Saitoh et al. | ................. | 600/459 |
| 5,497,540 A * | 3/1996 | Venkataramani et al. | ... | 29/25.35 |
| 5,552,004 A * | 9/1996 | Lorraine et al. | ............... | 156/154 |
| 5,637,800 A * | 6/1997 | Finsterwald et al. | ............ | 73/642 |
| 5,648,941 A * | 7/1997 | King | ............................ | 367/176 |
| 5,648,942 A * | 7/1997 | Kunkel, III | ................... | 367/176 |
| 5,651,365 A * | 7/1997 | Hanafy et al. | ................ | 600/459 |
| 5,654,101 A * | 8/1997 | Lorraine et al. | ................ | 428/398 |
| 5,655,276 A * | 8/1997 | Pattanayak et al. | ......... | 29/25.35 |
| 5,736,100 A * | 4/1998 | Miyake et al. | ................. | 422/64 |
| 5,916,169 A * | 6/1999 | Hanafy et al. | ................ | 600/459 |
| 6,020,675 A * | 2/2000 | Yamashita et al. | ............ | 310/358 |
| 6,045,208 A * | 4/2000 | Hirahara et al. | ................ | 347/10 |
| 6,051,913 A * | 4/2000 | King | ............................ | 310/327 |
| 6,087,762 A * | 7/2000 | Corbett et al. | ................ | 310/334 |
| 6,161,437 A * | 12/2000 | Brennan et al. | ................ | 73/655 |
| 6,244,101 B1 * | 6/2001 | Autrey et al. | ................ | 73/61.45 |
| 6,244,738 B1 * | 6/2001 | Yasuda et al. | ................. | 366/114 |
| 6,341,408 B2 * | 1/2002 | Bureau et al. | ............... | 29/25.35 |
| 6,396,198 B1 * | 5/2002 | Okimura et al. | ............ | 310/334 |
| 6,413,783 B1 * | 7/2002 | Wohlstadter et al. | ......... | 436/517 |
| 6,429,574 B1 * | 8/2002 | Mohr et al. | ................. | 310/334 |
| 6,489,706 B2 * | 12/2002 | Sliwa et al. | ................. | 310/334 |
| 6,552,471 B1 * | 4/2003 | Chandran et al. | ............ | 310/328 |
| 6,686,195 B1 * | 2/2004 | Colin et al. | ................ | 435/306.1 |
| 6,777,245 B2 * | 8/2004 | Wixforth | ...................... | 436/180 |
| 6,939,032 B2 * | 9/2005 | Cosby et al. | .................. | 366/114 |
| 7,808,642 B2 * | 10/2010 | Connelly et al. | ............. | 356/440 |
| 2001/0042289 A1 * | 11/2001 | Bureau et al. | ................ | 29/25.35 |
| 2001/0055529 A1 * | 12/2001 | Wixforth | ........................ | 417/53 |
| 2002/0026833 A1 * | 3/2002 | Autrey et al. | ................... | 73/643 |
| 2002/0042577 A1 * | 4/2002 | Hatangadi et al. | ............ | 600/459 |
| 2002/0044171 A1 * | 4/2002 | Hirahara et al. | ................ | 347/46 |
| 2003/0008296 A1 | 1/2003 | Hori et al. | | |
| 2003/0009873 A1 * | 1/2003 | Hatangadi et al. | ............. | 29/594 |
| 2004/0066313 A1 * | 4/2004 | Ong et al. | ................ | 340/870.11 |
| 2004/0115097 A1 * | 6/2004 | Wixforth et al. | ............. | 422/100 |
| 2006/0078473 A1 * | 4/2006 | Murakami | .................. | 422/100 |
| 2007/0002678 A1 * | 1/2007 | Murakami | .................. | 366/116 |
| 2008/0074945 A1 * | 3/2008 | Murakami et al. | ........... | 366/110 |
| 2008/0156078 A1 * | 7/2008 | Hsieh et al. | .................. | 73/54.02 |

FOREIGN PATENT DOCUMENTS

| | | | |
|---|---|---|---|
| JP | 08-146007 | | 6/1996 |
| JP | 2001-272404 | | 10/2001 |
| JP | 2002-257707 | | 9/2002 |
| JP | 2004-85443 | | 3/2004 |
| WO | WO 00 / 60049 | * | 10/2000 |
| WO | WO 03/018181 A1 | | 3/2003 |
| WO | WO 2004/076046 | | 9/2004 |

* cited by examiner

AGITATION VESSEL

TECHNICAL FIELD

The present invention relates to an agitation vessel, and more particularly to an agitation vessel which is employed in an agitation apparatus and an analysis apparatus.

BACKGROUND ART

A conventionally known agitator that agitates a liquid using sound waves is, for example, an agitator which is employed in a chemical analysis apparatus and includes a sound wave generator arranged outside a vessel retaining a liquid and agitates the liquid by directing the sound waves generated from the sound wave generator toward the vessel (see, for example, Patent Document 1).

Patent Document 1: Japanese Patent No. 3168886

DISCLOSURE OF INVENTION

Problem to be Solved by the Invention

An agitator disclosed in Patent Document 1 includes a sound wave generator arranged outside a vessel, and a constant-temperature water is arranged between the vessel and the sound wave generator and serves as an acoustic matching layer to maintain the temperature of the liquid at a constant level, whereby the vessel and the sound wave generator are distanced from each other. Therefore, when the agitator of Patent Document 1 is employed, sound waves generated from the sound wave generator are attenuated before reaching the vessel, whereby energy transmission efficiency is not favorable. Further, since the agitator of Patent Document 1 has a thermobath filled with the constant-temperature water, the agitator has a complicated configuration and bulky; and still further, the presence of the constant-temperature water complicates maintenance work.

In view of the foregoing, an object of the present invention is to provide an agitation vessel which allows for an improvement in the energy transmission efficiency of the agitation apparatus and analysis apparatus, allows for simplification of the configuration of the agitation apparatus and analysis apparatus so as to allow for downsizing and an improvement in maintenanceability thereof.

Means for Solving Problem

An agitation vessel according to one aspect of the present invention is for agitating retained liquid by sound waves, and includes a sound wave generating member integral with the agitation vessel, the sound wave generating member generating the sound waves.

Further, the agitation vessel may include a bottom wall and plural side walls made of an optically transparent material, and a part of the opposing side walls of the plural side walls may be a photometric window which is employed to optically measure the liquid agitated.

Further, in the agitation vessel, the sound wave generating member may be provided on the side wall, on which the photometric window is arranged, among the plural side walls.

Further, in the agitation vessel, the sound wave generating member may be provided at a portion other than a portion where the photometric window is provided in the side wall.

Further, in the agitation vessel, the sound wave generating member may be provided on the side wall other than the side wall, on which the photometric window is arranged, of the plural side walls, or on the bottom wall.

Further, in the agitation vessel, the sound wave generating member may be attached to a depressed portion formed on any of the plural side walls.

Further, in the agitation vessel, the sound wave generating member may constitute one of the bottom wall and the plural side walls.

Further, in the agitation vessel, the sound wave generating member may be in contact with the liquid.

Further, in the agitation vessel, the sound wave generating member may include on a substrate a sound wave generator having plural interdigital transducers of a surface-acoustic-wave element, and a power receiving unit which receives power transmitted from outside and transmits the power to the sound wave generator.

Further, in the agitation vessel, the sound wave generating member may be attached to the side wall or the bottom wall with the sound wave generator and the power receiver arranged inward.

Further, in the agitation vessel, the sound wave generating member may be attached to the side wall or the bottom wall with the sound wave generator and the power receiver arranged outward.

Further, in the agitation vessel, the sound wave generating member may be arranged on the bottom wall, and the sound wave generator may be arranged so that the plural interdigital transducers are aligned in a horizontal direction.

Further, in the agitation vessel, the sound wave generating member may be arranged on the side wall, and the sound wave generator may be arranged so that each of the plural interdigital transducers extends horizontally or extends in an inclined direction with respect to a horizontal direction, and the plural interdigital transducers may be arranged along a vertical direction or in an inclined direction with respect to the vertical direction.

Further, in the agitation vessel, the agitation vessel may include plural retaining portions that retain the liquid on an upper surface of a plate-like member formed of an optically transparent material, and the sound wave generating member may be provided on a surface of a bottom wall at a lower portion of each of the retaining portions.

Effect of the Invention

Since the agitation vessel according to the present invention has the integral sound wave generator, the transmission efficiency of energy from the sound wave generator to the agitation vessel is excellent. When used in the agitation apparatus or the analysis apparatus, the agitation vessel of the present invention improves the energy transmission efficiency of the agitation apparatus and the analysis apparatus, simplifies the configuration of the agitation apparatus and analysis apparatus enabling the downsizing and the improvement in maintenanceability.

| EXPLANATIONS OF LETTERS OR NUMERALS | |
|---|---|
| 1 | Automatic analysis apparatus |
| 2, 3 | Reagent table |
| 2a, 3a | Reagent vessel |
| 4 | Reaction table |
| 5 | Reaction vessel |
| 5a | Retaining portion |
| 5b | Photometric window |
| 5c | Side wall |
| 5d | Bottom wall |
| 5e | Depressed portion |
| 6, 7 | Reagent-dispensing mechanism |
| 8 | Specimen-vessel transfer mechanism |
| 9 | Feeder |
| 10 | Rack |
| 11 | Specimen-dispensing mechanism |
| 11a | Arm |
| 11b | Probe |
| 12 | Analytical optical system |
| 12a | Light-emitting portion |
| 12b | Spectral portion |
| 12c | Light-receiving portion |
| 13 | Washing mechanism |
| 13a | Nozzle |
| 15 | Control unit |
| 16 | Input unit |
| 17 | Display unit |
| 20 | Agitation apparatus |
| 21 | Power transmission element |
| 21a | Contact |
| 21b | Spring terminal |
| 22 | Positioning member |
| 24 | Surface-acoustic-wave element |
| 24a | Substrate |
| 24b | Sound wave generator |
| 24c | Electric terminal |
| 24d | Conductor circuit |
| 24e | Brush |
| 25 | Acoustic matching layer |
| 30 | Agitation apparatus |
| 31, 39 | Power transmission element |
| 31a | RF transmission antenna |
| 31b | Driving circuit |
| 31c | Controller |
| 33, 35 | Surface-acoustic-wave element |
| 33a, 35a | Substrate |
| 33b, 35b | Sound wave generator |
| 33c, 35c | Antenna |
| 34, 37 | Acoustic matching layer |
| 35d | Opening |
| 36, 41 | Surface-acoustic-wave element |

-continued

| EXPLANATIONS OF LETTERS OR NUMERALS | |
|---|---|
| 36a, 41a | Substrate |
| 36b, 41b | Sound wave generator |
| 36c | Antenna |
| 43, 45 | Surface-acoustic-wave element |
| 43a, 45a | Substrate |
| 43b, 45b | Sound wave generator |
| 47, 48 | Surface-acoustic-wave element |
| 47a, 48a | Substrate |
| 47b, 48b | Sound wave generator |
| 47c, 48c | Antenna |
| 50 | Agitation apparatus |
| 51 | Power transmission element |
| 51a | RF transmission antenna |
| 51b | Driving circuit |
| 51c | Controller |
| 53 | Surface-acoustic-wave element |
| 53a | Substrate |
| 53b | Sound wave generator |
| 53c | Antenna |
| 55 | Microplate |
| 55a | Main body |
| 55b | Well |
| 55c | Bottom surface |
| 55d | Vertex |
| Fcc, Fcw | Flow |
| Fd, Fu | Flow |

BEST MODE(S) FOR CARRYING OUT THE INVENTION

First Embodiment

Figure 1:
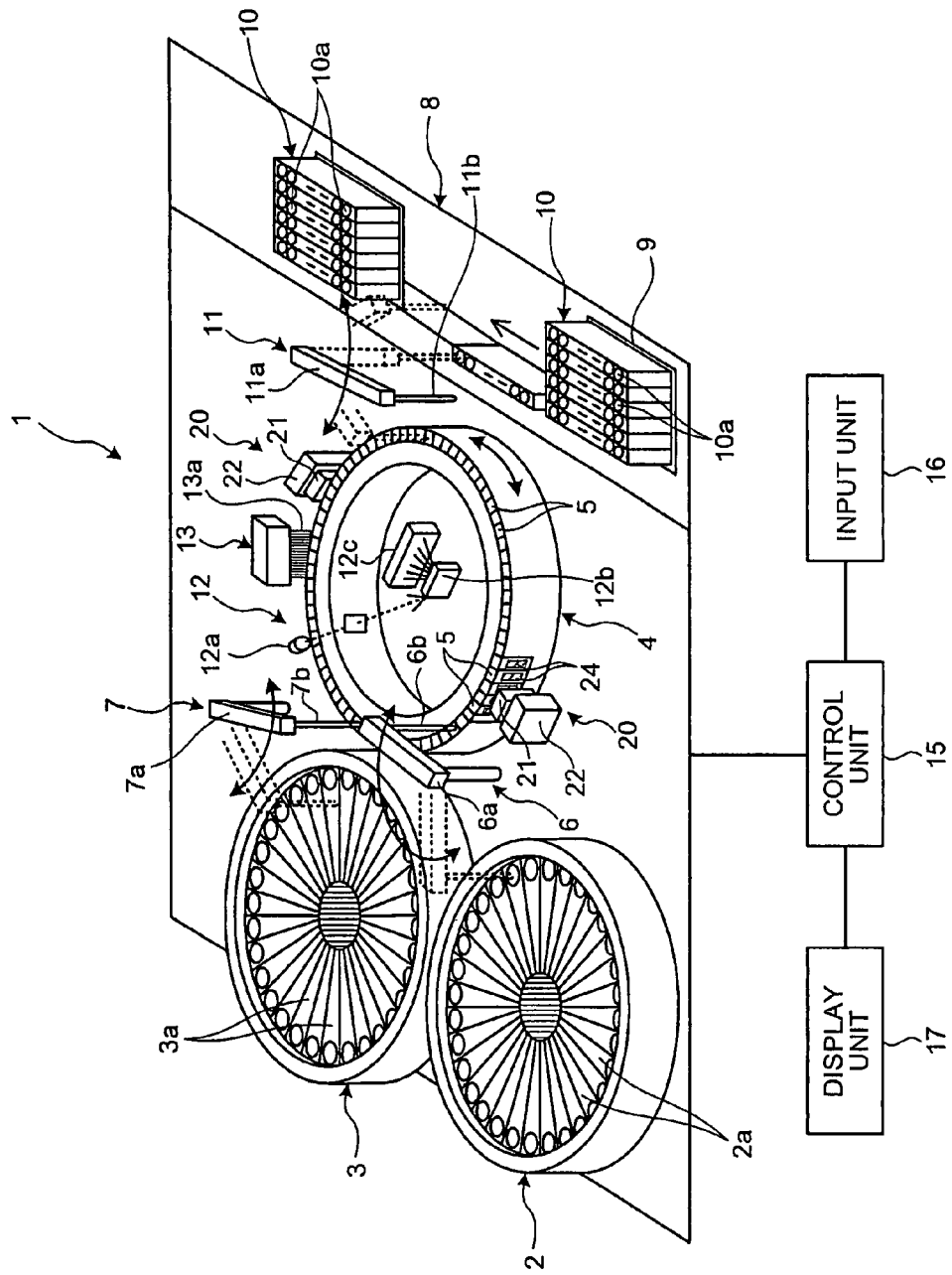
FIG. 1 shows a first embodiment of the present invention, and is a schematic configuration diagram of an automatic analysis apparatus including an agitation apparatus which agitates a liquid retained in an agitation vessel according to the first embodiment.
Figure 2:
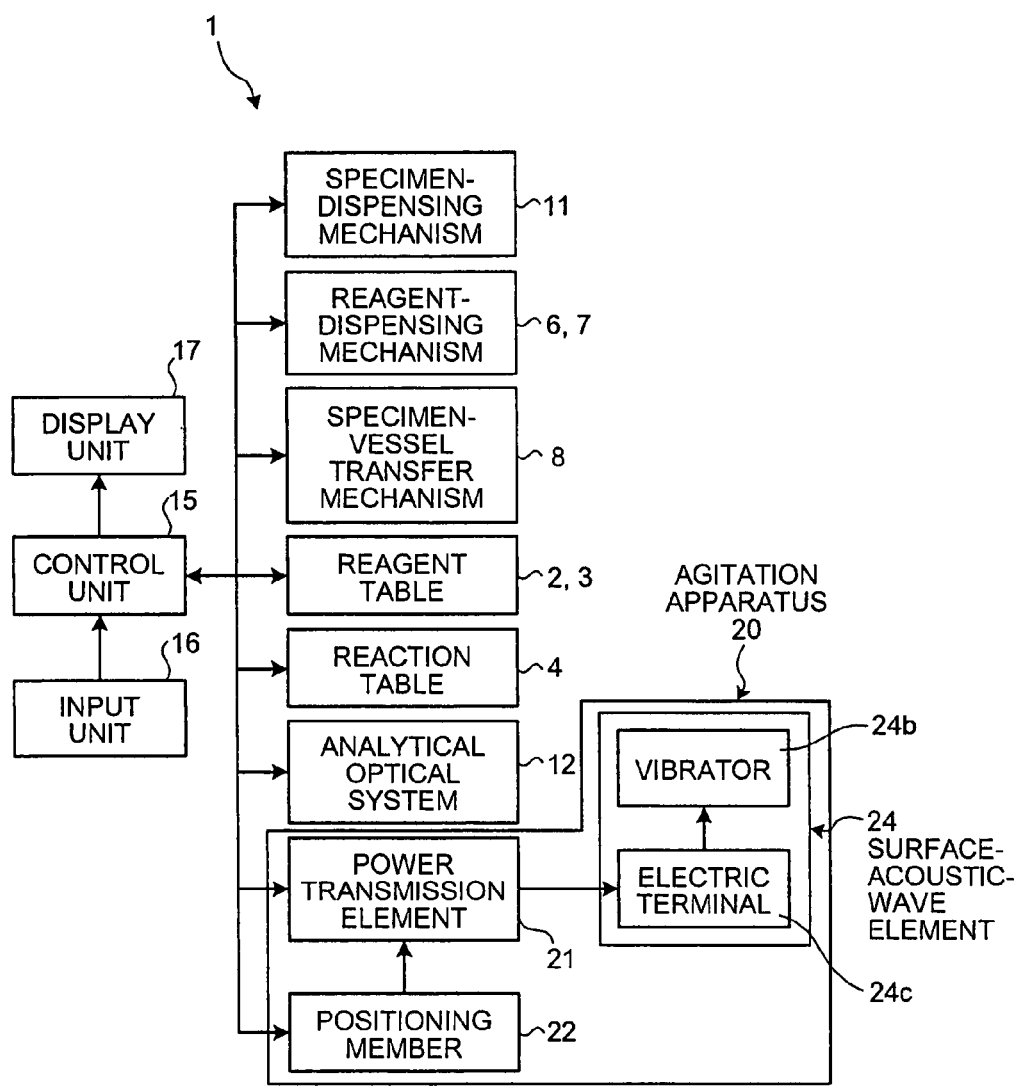
FIG. 2 is a block diagram of a configuration of the automatic analysis apparatus of FIG. 1.
Figure 3:
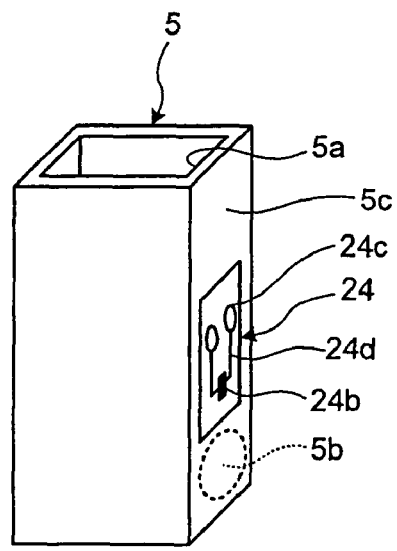
FIG. 3 is a perspective view of the agitation vessel which includes an integral sound wave generator and is employed in the automatic analysis apparatus of FIG. 1.

An agitation vessel according to a first embodiment of the present invention will be described in detail below with reference to the accompanying drawings in which an analysis apparatus including an agitation apparatus to agitate a liquid is also shown. FIG. 1 is a schematic configuration diagram of an automatic analysis apparatus including an agitation apparatus which agitates a liquid retained in the agitation vessel according to the first embodiment. FIG. 2 is a block diagram of a configuration of the automatic analysis apparatus of FIG. 1. FIG. 3 is a perspective view of the agitation vessel which is employed in the automatic analysis apparatus of FIG. 1 and includes an integral sound-wave generator.

An automatic analysis apparatus 1 includes reagent tables 2 and 3, a reaction table 4, a specimen-vessel transfer mechanism 8, an analytical optical system 12, a washing mechanism 13, a control unit 15, and an agitation apparatus 20 as shown in FIGS. 1 and 2.

As shown in FIG. 1, the reagent table 2 holds plural reagent vessels 2a circumferentially arranged, whereas the reagent table 3 holds plural reagent vessels 3a circumferentially arranged, and the reagent tables 2 and 3 are rotated by a driving unit (not shown) to transport the reagent vessels 2a and 3a in a circumferential direction.

In the reaction table 4, plural reaction vessels 5 are arranged along a circumferential direction as shown in FIG. 1. The reaction table 4 is rotated in a clockwise or counterclockwise direction as shown by an arrow by a driving unit (not shown) to transport the reaction vessels 5. Reagent-dispensing mechanisms 6 and 7 arranged close to the reaction vessel 5 dispense the reagent in each of the reagent vessels 2a and 3a on the reagent tables 2 and 3 to the reaction vessel 5. The reagent-dispensing mechanisms 6 and 7 respectively include probes 6b and 7b in arms 6a and 7a which rotate in directions of arrows in a horizontal plane to dispense the reagent, and further include a washer (not shown) that washes the probes 6b and 7b with washing water.

As shown in FIG. 3, the reaction vessel 5 is a rectangular-tube-like agitation vessel which is formed of an optically transparent material, and has a retaining portion 5a for retaining a liquid, and includes an integrally formed surface-acoustic-wave element 24 on one of plural side walls 5c. The reaction vessel 5 is made of a material which transmits at least 80% of light included in an analytical light (340 to 800 nm) emitted from the analytical optical system 12 described later. For example, the reaction vessel 5 is made of glass such as heat-resistant glass, synthetic resin such as cyclic olefin and polystyrene. The reaction vessel 5 has opposing side walls 5c and a portion which is enclosed by a dotted line and is located below and adjacent to a portion where the surface-acoustic-wave element 24 is attached is utilized as a photometric window 5b that transmits the analytic light. When the reaction vessel 5 is placed on the reaction table 4, the surface-acoustic-wave element 24 faces outward.

The specimen-vessel transfer mechanism 8 is a transfer unit which transfers plural racks 10 arranged on a feeder 9 one by one along a direction of an arrow as shown in FIG. 1, and advances the rack 10 stepwise. The rack 10 holds plural specimen vessels 10a each retain a specimen. Whenever the stepwise advancement of the rack 10 which is transferred by the specimen-vessel transfer mechanism 8 is stopped, a specimen-dispensing mechanism 11 having an arm 11a which rotates in a horizontal direction and a probe 11b dispenses the specimen in the specimen vessel 10a into each of the reaction vessels 5. The specimen-dispensing mechanism 11 has a washer (not shown) to wash the probe 11b with washing water.

The analytical optical system 12 serves to emit the analytical light (340 to 800 nm) for an analysis of the liquid sample obtained as a result of reaction between the reagent and the specimen in the reaction vessel 5, and includes a light-emitting portion 12a, a spectral portion 12b, and a light-receiving portion 12c, as shown in FIG. 1. The analytical light emitted from the light-emitting portion 12a passes through the liquid sample in the reaction vessel 5 and is received by the light-receiving portion 12c which is arranged at a position opposing to the spectral portion 12b. The light-receiving portion 12c is connected to the control unit 15.

The washing mechanism 13 washes the reaction vessel 5 after the analytical optical system 12 finishes the analysis, by aspirating and discharging the liquid sample in the reaction vessel 5 through a nozzle 13a, and repeatedly injecting and aspirating a washing agent or washing water through the nozzle 13a.

The control unit 15 controls an operation of each portion of the automatic analysis apparatus 1, and at the same time, analyzes components, concentration, and the like of the specimen based on absorbance of the liquid sample in the reaction vessel 5 based on quantity of light emitted from the light-emitting portion 12a and quantity of light received by the light-receiving portion 12c. For example, a micro computer is employed as the control unit 15. The control unit 15 is, as shown in FIGS. 1 and 2, connected to an input unit 16 such as a keyboard, and a display unit 17 such as a display panel.

Figure 4:
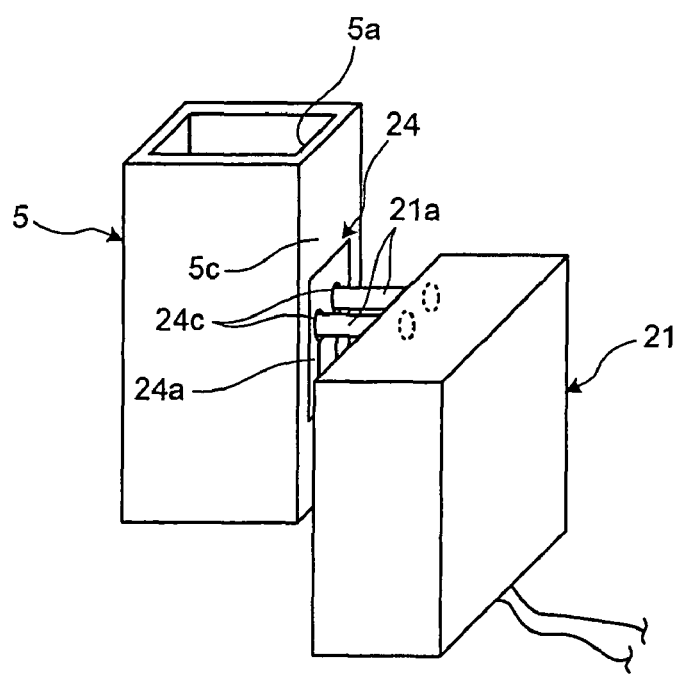
FIG. 4 is a perspective view showing a state in which a power transmission element contacts an electric terminal of a surface-acoustic-wave element of the agitation vessel via a contact.

The agitation apparatus 20 includes, as shown in FIGS. 1 and 2, a power transmission element 21 and the surface-acoustic-wave element 24. The power transmission elements 21 are arranged at opposing positions on an outer circumferentia of the reaction table 4, so that the power transmission element 21 is placed opposite to the reaction vessel 5 in a horizontal direction; and the power transmission element 21 is a power transmitter which transmits approximately a few MHz to a few hundreds MHz power supplied from a high-frequency alternate-current power supply to the surface-acoustic-wave element 24. The power transmission element 21 includes a driving circuit and a controller, and has brush-like contacts 21a respectively touching electric terminals 24c of the surface-acoustic-wave element 24, as shown in FIG. 4. As shown in FIG. 1, the power transmission element 21 is supported by a positioning member 22. When the rotation of the reaction table 4 stops, power is transmitted from the contact 21a to the electric terminal 24c.

An operation of the positioning member 22 is controlled by the control unit 15, and the positioning member 22 serves to determine relative arrangement of the power transmission element 21 and the electric terminal 24c in the circumferential direction and the radial direction of the reaction table 4 at a time of power transmission from the power transmission element 21 to the electric terminal 24c. For example, a biaxial stage is employed as the positioning member 22. Specifically, in a non-power-transmission time, during which the reaction table 4 rotates and the power is not transmitted from the power transmission element 21 to the electric terminal 24c, the operation of the positioning member 22 is stopped, and the power transmission element 21 and the electric terminal 24c are kept at a predetermined distance away from each other. In a power-transmission time, during which the reaction table 4 stops and the power is transmitted from the power transmission element 21 to the electric terminal 24c, the positioning member 22 operates under the control of the control unit 15 so as to determine the positions of the power transmission element 21 and the electric terminal 24c in the circumferential direction of the reaction table 4 so that the power transmission element 21 opposes the electric terminal 24c, thereby bringing the power transmission element 21 in close contact with the electric terminal 24c and making the contact 21a and the electric terminal 24c contact with each other. The agitation apparatus 20 may use the control unit 15 of the automatic analysis apparatus 1 as a positioner, and control a driving unit such as a motor that drives the rotation of the reaction table 4 by the control unit 15 so as to determine the relative arrangement of the power transmission element 21 and the electric terminal 24c along the circumferential direction of the reaction table 4. It is sufficient if the positioning member 22 can determine the arrangement of the power transmission element 21 and the electric terminal 24c at least in the circumferential direction of the reaction table 4 so that the power transmission element 21 and the electric terminal 24c oppose with each other. The relative arrangement of the power transmission element 21 and the electric terminal 24c is detected by a reflection sensor arranged at the side of the power transmission element 21, with the use of reflection from a reflector arranged at a specific position on the reaction vessel 5 or the surface-acoustic-wave element 24, for example. Data on the detected relative arrangement is input into the control unit 15.

Figure 5:
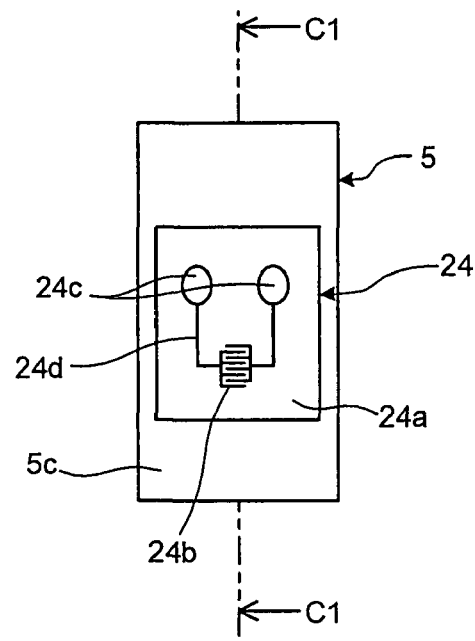
FIG. 5 is a side view of the agitation vessel of FIG. 4 viewed from one side where the surface-acoustic-wave element is provided.
Figure 6:
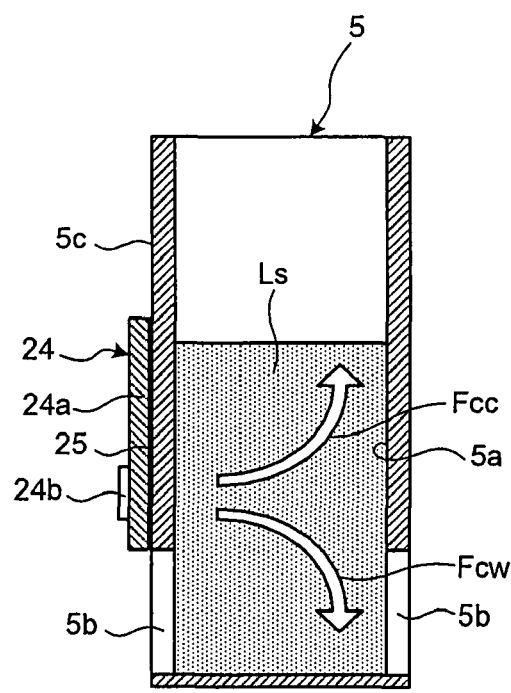
FIG. 6 is a sectional view of the agitation vessel along line C1-C1 of FIG. 4, illustrating flows of liquid sample in section.

The surface-acoustic-wave element 24 is a sound-wave generating member, and includes a sound wave generator 24b including interdigital transducers (IDT) arranged on a surface of a substrate 24a, as shown in FIGS. 3 and 5. The sound wave generator 24b is a sound-wave generator which converts the power transmitted from the power transmission element 21 into surface acoustic waves (ultrasound waves). Plural interdigital transducers are arranged in a vertical direction on the side wall 5c of the reaction vessel 5 as shown in FIG. 5 so that the surface acoustic waves (ultrasound waves) are generated in the vertical direction. In other words, the surface-acoustic-wave element 24 is attached onto the side wall 5c of the reaction vessel 5 so that the plural interdigital transducers of the sound wave generator 24b are arranged in the vertical direction when the reaction vessel 5 is set in the automatic analysis apparatus 1. The sound wave generator 24b is connected through a conductor circuit 24d to the electric terminal 24c that serves as a power receiver. The surface-acoustic-wave element 24 is attached onto the side wall 5c of the reaction vessel 5 with an acoustic matching layer 25 (see FIG. 6) of epoxy resin or the like posed therebetween, while the sound wave generator 24b, the electric terminal 24c, and the conductor circuit 24d are kept facing outward. The surface-acoustic-wave element 24 including the electric terminal 24c as the power receiver is arranged at a portion other than the photometric window 5b portion on the same side surface of the reaction vessel 5 as the side where the photometric window 5b is arranged as shown in FIG. 3, so that the photometry of the analytical optical system 12 is not obstructed. Since the surface-acoustic-wave element 24 employs the interdigital transducers (IDT) as the sound wave generator 24b, the surface-acoustic-wave element 24 can be made to have a simplified configuration and a small size. The surface-acoustic-wave element 24 may employ a Lead Zirconate Titanate (PZT) substrate, a zinc oxide (ZnO) substrate, a silicon substrate, or the like in place of the interdigital transducers (IDT).

In the automatic analysis apparatus 1 having the above-described configuration, the reagent-dispensing mechanisms 6 and 7 sequentially dispense the reagent from the reagent vessels 2a and 3a to the plural reaction vessels 5 that are transferred in the circumferential direction along with the rotation of the reaction table 4. After the reagent is dispensed into the reaction vessel 5, the specimen-dispensing mechanism 11 sequentially dispenses the specimen from the plural specimen vessels 10a held in the rack 10. Every time the reaction table 4 is stopped, the reagent and the specimen dispensed into the reaction vessel 5 are sequentially agitated by the agitation apparatus 20 and undergo reaction. When the reaction table 4 starts rotating again, the reaction vessel 5 passes through the analytical optical system 12. Thereupon, the light-receiving portion 12c performs photometry of the liquid sample in the reaction vessel 5. Then, the control unit 15 analyzes the components, concentration, and the like. After the analysis is completed, the washing mechanism 13 washes the reaction vessel 5, which is then employed for the analysis of the specimen again.

In the agitation apparatus 20, the power transmission element 21 transmits the power via the contact 21a to the electric terminal 24c when the reaction table 4 stops. Accordingly, the sound wave generator 24b of the surface-acoustic-wave element 24 is driven to induce surface acoustic waves. The induced surface acoustic waves propagate through the acoustic matching layer 25 and the side wall 5c of the reaction vessel 5, and leak out into the liquid sample which has close acoustic impedance. As a result, a counterclockwise flow Fcc and a clockwise flow Fcw are generated respectively at an upper portion and a lower portion in a liquid sample Ls in the reaction vessel 5, each originating from a position corresponding to the sound wave generator 24b as shown by arrows, in FIG. 6. Two flows agitate the reagent and the specimen dispensed in the reaction vessel 5. Since the agitation apparatus 20 positions the elements using the positioning member 22 so as to bring the power transmission element 21 and the electric terminal 24c in close contact with each other, and to place the power transmission element 21 and the electric terminal 24c opposite to each other, the power transmission can be performed smoothly from the power transmission element 21 to the electric terminal 24c.

The surface-acoustic-wave element 24 is attached firmly to the side wall 5c of the reaction vessel 5 in an integral manner with the acoustic matching layer 25 (see FIG. 6) placed therebetween, and a bath retaining constant-temperature water is not employed. Therefore, the ultrasound waves generated by the surface-acoustic-wave element 24 propagate through the acoustic matching layer 25 and the side wall 5c, and are scarcely attenuated, thus the reaction vessel 5 has excellent energy transmission efficiency and a simplified configuration. As can be seen, the use of the reaction vessel 5 in the agitation apparatus 20 and the automatic analysis apparatus 1 allows for downsizing and simplified maintenance work compared with a conventional analysis apparatus which includes a bath retaining the constant-temperature water as the acoustic matching layer.

Figure 7:
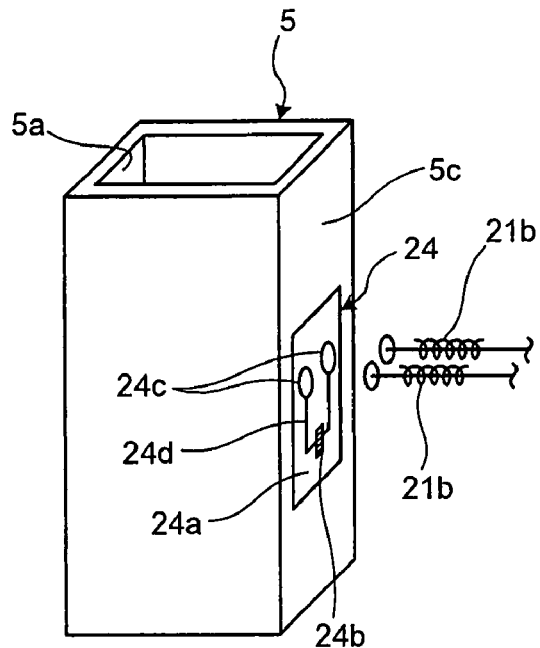
FIG. 7 is a perspective view of a modified example of a power transmission element including spring terminals in place of the contacts, and the vessel.

In the first embodiment, the agitation apparatus 20 is configured so that the power transmission element 21 contacts with the electric terminal 24c via the brush-like contact 21a to transmit power to the surface-acoustic-wave element 24. The agitation apparatus 20, however, may be configured so that at the power transmission to the surface-acoustic-wave element 24, the positioning member 22 having a rack and a pinion brings the power transmission element 21 closer to the reaction vessel 5 after the reaction table 4 is stopped, and makes a spring terminal 21b provided in the power transmission element 21 contact with the electric terminal 24c, as shown in FIG. 7. When the agitation apparatus 20 has the above configuration, the automatic analysis apparatus 1 keeps the power transmission element 21 away from the reaction vessel 5 using the positioning member 22 when the reaction table 4 is rotated for the transfer of the reaction vessel 5 so as to prevent the interference between the spring terminal 21b and the surface-acoustic-wave element 24.

Alternatively, the power transmission element 21 may be arranged inside the reaction table 4 together with the positioning member 22 in such a manner that at least the power transmission to the surface-acoustic-wave element 24 is allowed. The reaction vessel 5 may be set in the reaction table 4 with the surface where the surface-acoustic-wave element 24 is attached is kept facing inward.

Figure 8:
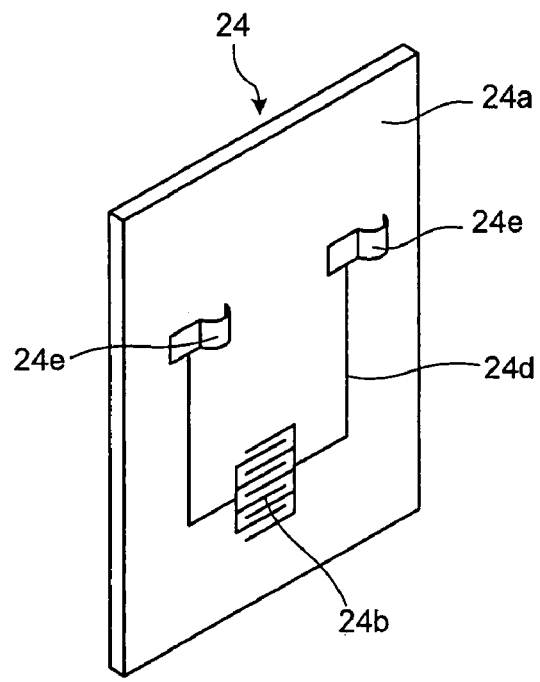
FIG. 8 is a perspective view of a modified example of a surface-acoustic-wave element.

On the other hand, the surface-acoustic-wave element 24 may be provided with a brush 24e formed with a flat spring deformed to have a curved protrusion in place of the electric terminal 24c as shown in FIG. 8. The power transmission element 21 may be provided with a terminal where the brush 24e touches as the reaction table 4 rotates. With such a configuration of the automatic analysis apparatus 1, when the reaction table 4 stops, the brush 24e integrally provided on the reaction vessel 5 comes into contact with the terminal of the power transmission element 21. Thus, the agitation apparatus 20 can transmit power from the power transmission element 21 to the surface-acoustic-wave element 24 via the brush 24e.

Second Embodiment

Figure 9:
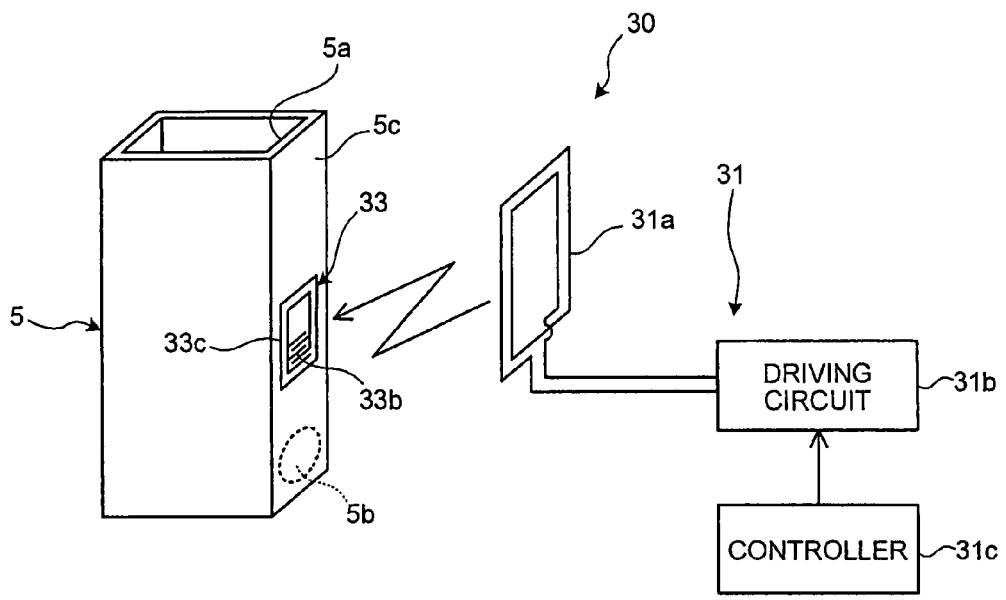
FIG. 9 shows a second embodiment of the present invention, and is a block diagram of a configuration of an agitation apparatus which agitates a liquid retained in an agitation vessel according to the second embodiment.
Figure 10:
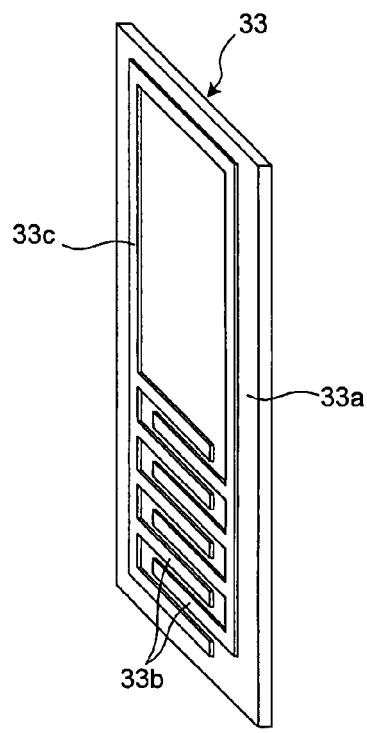
FIG. 10 is a perspective view of a surface-acoustic-wave element attached to a reaction vessel in the agitation apparatus of FIG. 9.

An agitation vessel according to a second embodiment of the present invention will be described in detail with reference to the accompanying drawings. The agitation vessel according to the first embodiment is described as being used in the agitation apparatus which transmits power by bringing the power transmission element and the electric terminal of the surface-acoustic-wave element into contact with each other. On the other hand, as described below, the agitation vessel according to the second embodiment is used in an agitation apparatus which transmits power using an antenna while keeping the power transmission element and the surface-acoustic-wave element in a non-contact state. FIG. 9 is a block diagram showing a configuration of the agitation apparatus which agitates a liquid retained in the agitation vessel according to the second embodiment. FIG. 10 is a perspective view of the surface-acoustic-wave element attached to the reaction vessel in the agitation apparatus of FIG. 9.

An agitation apparatus 30 has a power transmission element 31 which serves as a power transmitter and a surface-acoustic-wave element 33, as shown in FIG. 9. The surface-acoustic-wave element 33 is attached to the side wall 5c, in which the photometric window 5b is formed, of the reaction vessel 5 in an integral manner.

The power transmission element 31 is supported by the positioning member 22 similarly to the power transmission element 21, so that the power transmission elements 31 are placed at opposing positions on the outer circumferentia of the reaction table 4 horizontally opposing to the reaction vessel 5. The power transmission element 31 is arranged opposite to the surface-acoustic-wave element 33, and includes an RF transmission antenna 31a, a driving circuit 31b, and a controller 31c. The power transmission element 31 transmits the power of an approximately few MHz to a few hundred MHz supplied from a high-frequency alternate-current power supply to the surface-acoustic-wave element 33 via the RF transmission antenna 31a as electric waves. When the power transmission element 31 is to transmit the power to the surface-acoustic-wave element 33, the positioning member 22 determines the relative arrangement of the power transmission element 31 with respect to the reaction table 4 in a circumferential direction and a radial direction so that the RF transmission antenna 31a and an antenna 33c are opposing to each other. The relative arrangement of the RF transmission antenna 31a and the antenna 33c is detected with the use of, for example, a reflection sensor provided at the power transmission element 31 side and reflection from a reflector provided at a specific position on the reaction vessel 5 or the surface-acoustic-wave element 33.

The surface-acoustic-wave element 33 is a sound wave generating member, and includes a sound wave generator 33b including interdigital transducers (IDT) provided on the surface of a substrate 33a as an integral part of the antenna 33c as shown in FIG. 10. The surface-acoustic-wave element 33 is attached to the side wall 5c of the reaction vessel 5 with an acoustic matching layer 34 (see FIGS. 11 and 12) made of epoxy resin or the like posed therebetween, while the sound wave generator 33b and the antenna 33c are kept facing outward. As shown in FIG. 9, the surface-acoustic-wave element 33 is attached to the reaction vessel 5 so that the plural interdigital transducers of the sound wave generator 33b are arranged in the vertical direction in a position other than a position where the photometric window 5b is provided on the same side surface as the photometric window 5b is provided. Using the interdigital transducers (IDT) as the sound wave generator 33b, the surface-acoustic-wave element 33 is allowed to have a simplified configuration and small size. The surface-acoustic-wave element 33 receives the electric waves transmitted from the power transmission element 31 to the antenna 33c to generate the surface acoustic waves (ultrasound waves) from the sound wave generator 33b according to the electromotive force caused by the resonance.

In the agitation apparatus 30 having the above-described configuration, the power transmission element 31 transmits the electric waves from the RF transmission antenna 31a when the reaction table 4 stops and the RF transmission antenna 31a and the antenna 33c come to oppose with each other. Then, the antenna 33c of the surface-acoustic-wave element 33 placed opposite to the power transmission element 31 receives the electric waves to generate the electromotive force by the resonance. In the agitation apparatus 30, the sound wave generator 33b generates the surface acoustic waves (ultrasound waves) according to the electromotive force, and the surface acoustic waves propagate through the acoustic matching layer 34 to the inside of the side wall 5c of the reaction vessel 5, and eventually leak out to the liquid sample which has a close acoustic impedance. As a result, a counterclockwise flow Fcc and a clockwise flow Fcw are generated respectively in an upper portion and a lower portion as shown by arrows of FIG. 11 in the liquid sample Ls of the reaction vessel 5, originating from a position corresponding to the sound wave generator 33b, whereby the dispensed reagent and the specimen are agitated.

As described above, in the agitation apparatus 30, the non-contact power transmission from the power transmission element 31 to the surface-acoustic-wave element 33 attached to the reaction vessel 5 is achieved with the RF transmission antenna 31a and the antenna 33c, and the sound wave generator 33b is integrally formed on the reaction vessel 5. Therefore, the reaction vessel 5 of the second embodiment, similarly to the reaction vessel 5 of the first embodiment, has excellent energy transmission efficiency and does not include a bath retaining the constant-temperature water, whereby the maintenance of the agitation apparatus 30 is readily achieved, the structure of the surface-acoustic-wave element 33 is further simplified and downsized compared with the corresponding element in the agitation apparatus 20, and as a result, the automatic analysis apparatus 1 can be further downsized.

Figure 13:
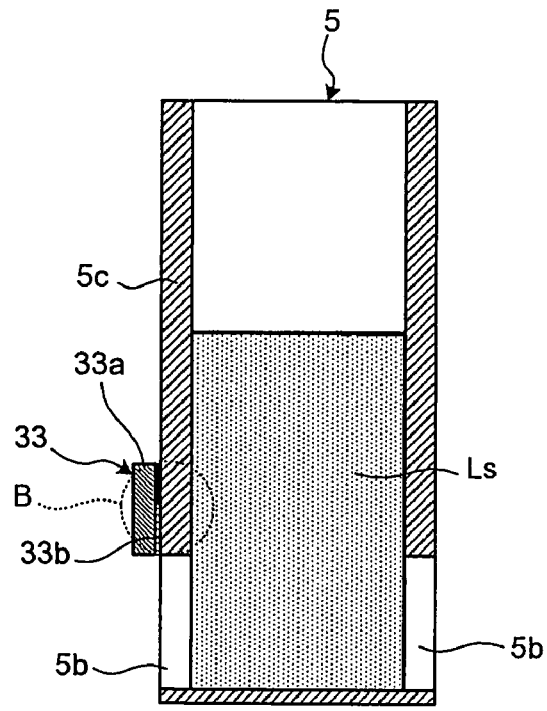
FIG. 13 is a sectional view illustrating another manner of attachment of the surface-acoustic-wave element.
Figure 14:
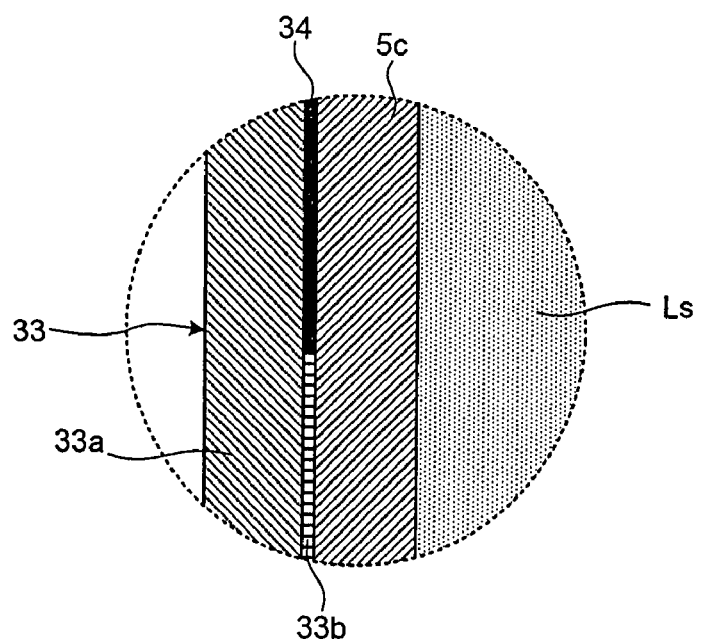
FIG. 14 is an enlarged view of a B-portion of FIG. 13.

Since the surface-acoustic-wave element 33 employs the interdigital transducers (IDT) as the sound wave generator 33b, the configuration thereof is simplified, and in particular, a portion of the sound wave generator 33b can be made thin. Therefore, the surface-acoustic-wave element 33 may be attached to the side wall 5c with the sound wave generator 33b facing inward as shown in FIG. 13. As shown in FIG. 14, the acoustic matching layer 34 is placed between the surface-acoustic-wave element 33 and the side wall 5c. Thus, in the reaction vessel 5, the sound wave generator 33b, the antenna 33c, and the like of the surface-acoustic-wave element 33 are not exposed to the outside and protected by the substrate 33a, whereby the degradation of the surface-acoustic-wave element 33 can be suppressed in comparison with the surface-acoustic-wave element having the sound wave generator 33b, the antenna 33c, and the like arranged outside, and the long-term use can be realized.

Figure 15:
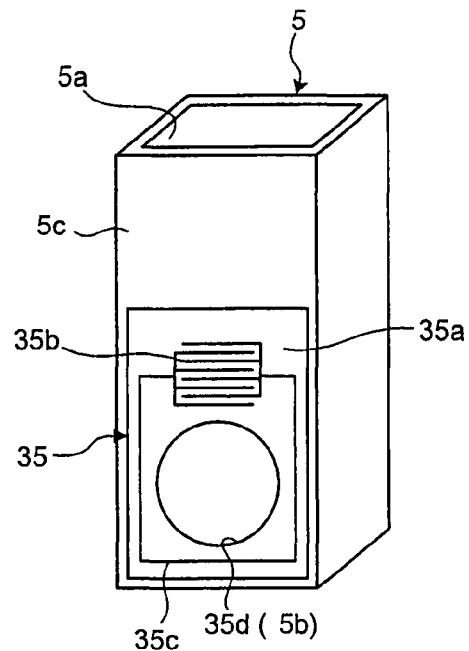
FIG. 15 is a perspective view of a vessel showing another mode of the surface-acoustic-wave element.

In the reaction vessel 5, the surface-acoustic-wave element 33 is arranged on the same side surface as that on which the photometric window 5b is arranged. In consideration of the analysis of the liquid sample by the analytic optical system 12 of the automatic analysis apparatus 1, however, the surface-acoustic-wave element 33 needs to be arranged at a portion other than the portion where the photometric window 5b is provided. However, since the reaction vessel 5 has a little capacity, an area where the surface-acoustic-wave element 33 can be arranged is limited. Therefore, as exemplified by a surface-acoustic-wave element 35 shown in FIG. 15, an opening 35d may be provided in a substrate 35a of a surface-acoustic-wave element at a position corresponding to the window 5b of the reaction vessel 5, and an antenna 35c may be arranged around the opening 35d and formed integrally with a sound wave generator 35b. The opening 35d is aligned with the position of the window 5b of the reaction vessel 5, and the surface-acoustic-wave element is attached to the reaction vessel 5 with the acoustic matching layer (not shown) of epoxy resin or the like placed therebetween. With the above configuration of the reaction vessel 5, even though the surface-acoustic-wave element 33 is arranged on the same side surface as that on which the photometric window 5b is provided, the antenna 35c is arranged at a portion other than the portion where the photometric window 5b is provided in the reaction vessel 5, and the plural interdigital transducers of the sound wave generator 35b are arranged in the vertical direction. Thus, regardless of the small capacity of the reaction vessel 5, an optical path for photometry by the analytic optical system 12 can be secured.

Figure 16:
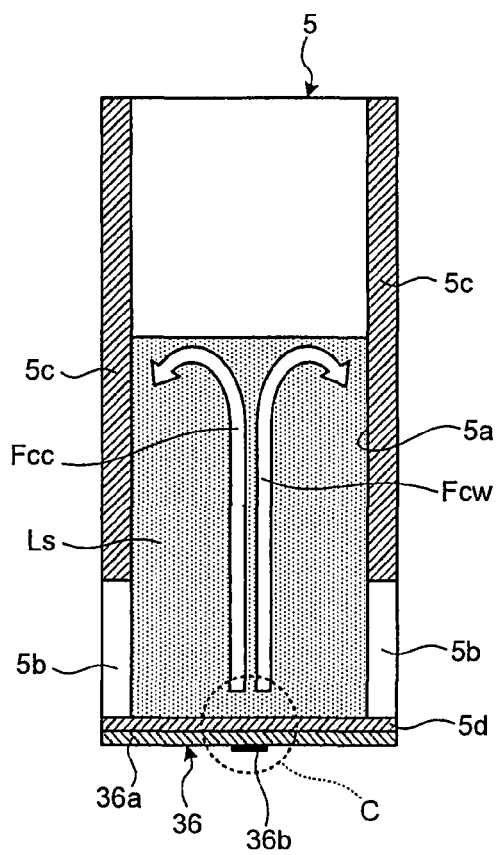
FIG. 16 is a sectional view illustrating flows of a liquid sample along a section of the vessel, the surface-acoustic-wave element being attached to the bottom surface of the vessel.
Figure 17:
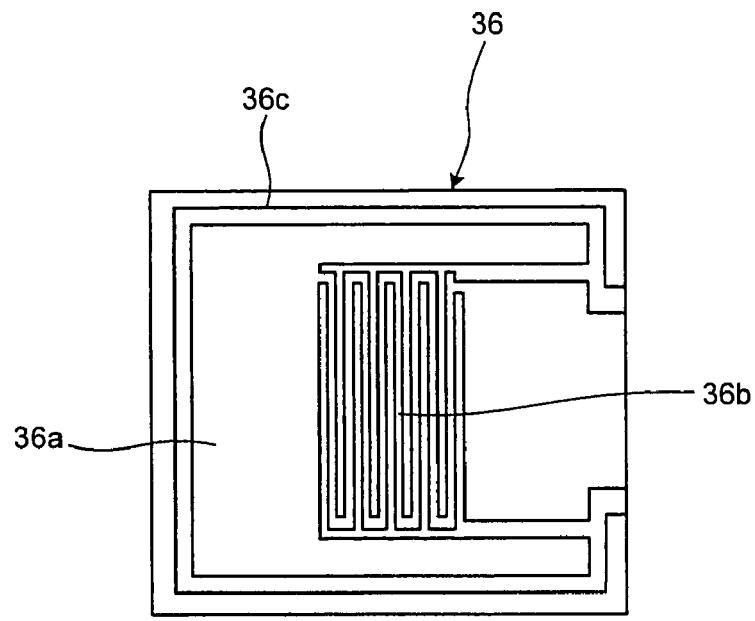
FIG. 17 shows the surface-acoustic-wave element shown in FIG. 16 viewed from the bottom surface of the vessel.
Figure 18:
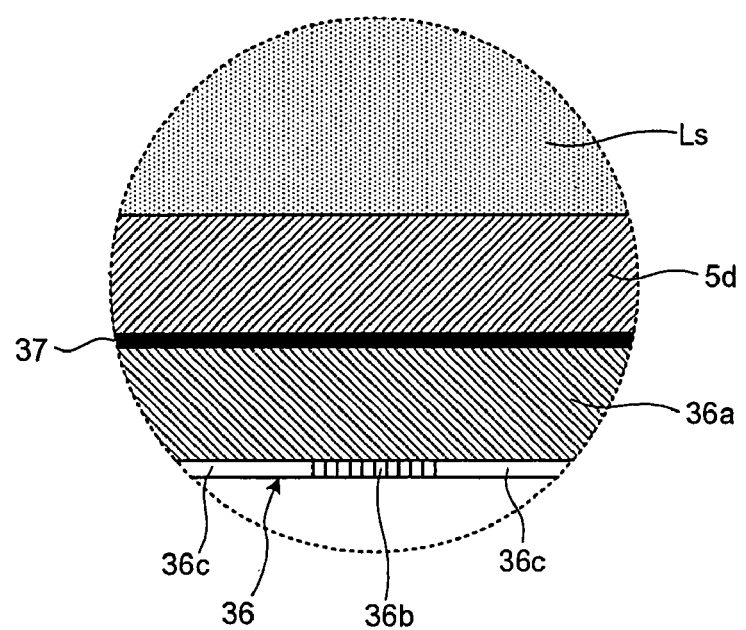
FIG. 18 is an enlarged view of a C-portion of FIG. 16.

Further, since the agitation apparatus 30 can transmit the power in the non-contact manner, there is an increased degree of freedom with respect to the attachment position of the surface-acoustic-wave element on the reaction vessel 5. Hence, a surface-acoustic-wave element 36 may be attached to the bottom surface of the bottom wall 5d of the reaction vessel 5 as shown in FIG. 16, and not on the same side surface as that on which the photometric window 5b is provided. As shown in FIG. 17, in the surface-acoustic-wave element 36, a sound wave generator 36b including the interdigital transducers (IDT) is formed integrally with an antenna 36c which serves as a power receiver on the surface of a substrate 36a. As shown in FIG. 18, the surface-acoustic-wave element 36 is attached to the bottom surface of the bottom wall 5d via an acoustic matching layer 37 of epoxy resin or the like. Thus in the surface-acoustic-wave element 36, the plural interdigital transducers of the sound wave generator 36b are arranged in a horizontal direction. Therefore, when the power is transmitted from the power transmission element 31 in a non-contact manner, a counterclockwise flow Fcc and a clockwise flow Fcw are generated respectively at the left side and the right side in the liquid sample Ls in the reaction vessel 5 originating from a position corresponding to the sound wave generator 36b as shown by arrows in FIG. 16, and the dispensed reagent and the specimen are agitated.

Figure 19:
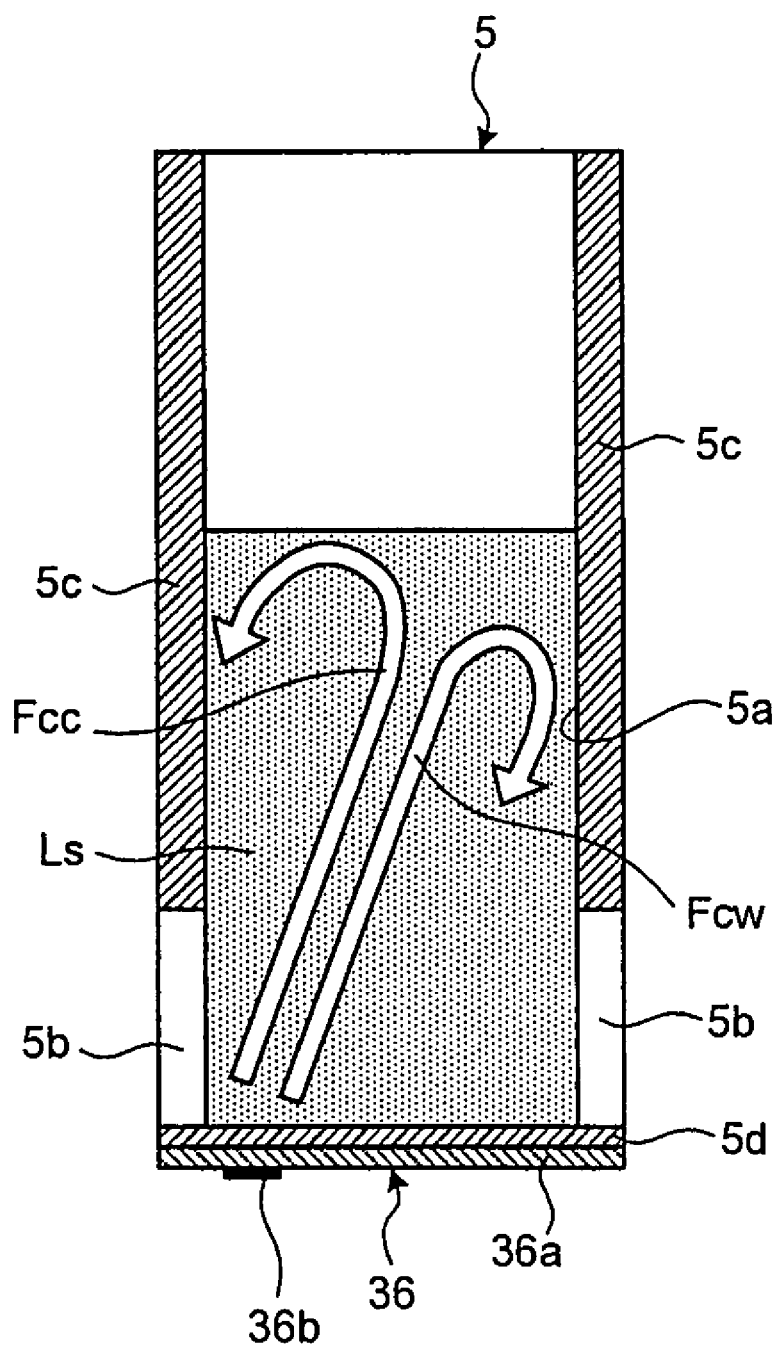
FIG. 19 is a sectional view illustrating flows of a liquid sample along a section of the vessel which includes a surface-acoustic-wave element having a sound wave generator at a shifted position.

As shown in FIG. 19, in the surface-acoustic-wave element 36, the sound wave generator 36b may be arranged closer to one side on the surface of the substrate 36a so that the sound wave generator comes close to the side of one of the side walls 5c of the reaction vessel 5. When the surface-acoustic-wave element 36 has the position-shifted sound wave generator 36b, the counterclockwise flow Fcc and the clockwise flow Fcw that move diagonally upward, rightward direction originating from a point close to the sound wave generator 36b are generated in the liquid sample Ls of the reaction vessel 5. When the power is transmitted from the power transmission element 31 to the reaction vessel 5 in a non-contact manner, the liquid sample Ls is agitated by flows Fcc and Fcw of two directions; in particular, even if there is a meniscus, a wide portion including a portion of meniscus can be agitated.

After the agitation and reaction of the reagent and the specimen, the light-receiving portion 12c of the automatic analysis apparatus 1 performs photometry of the liquid sample, and the control unit 15 analyzes the components, concentration, and the like of the liquid sample. After the analysis is finished, the reaction vessel 5 is washed by the washing mechanism 13 and employed for the analysis of the specimen again.

Figure 20:
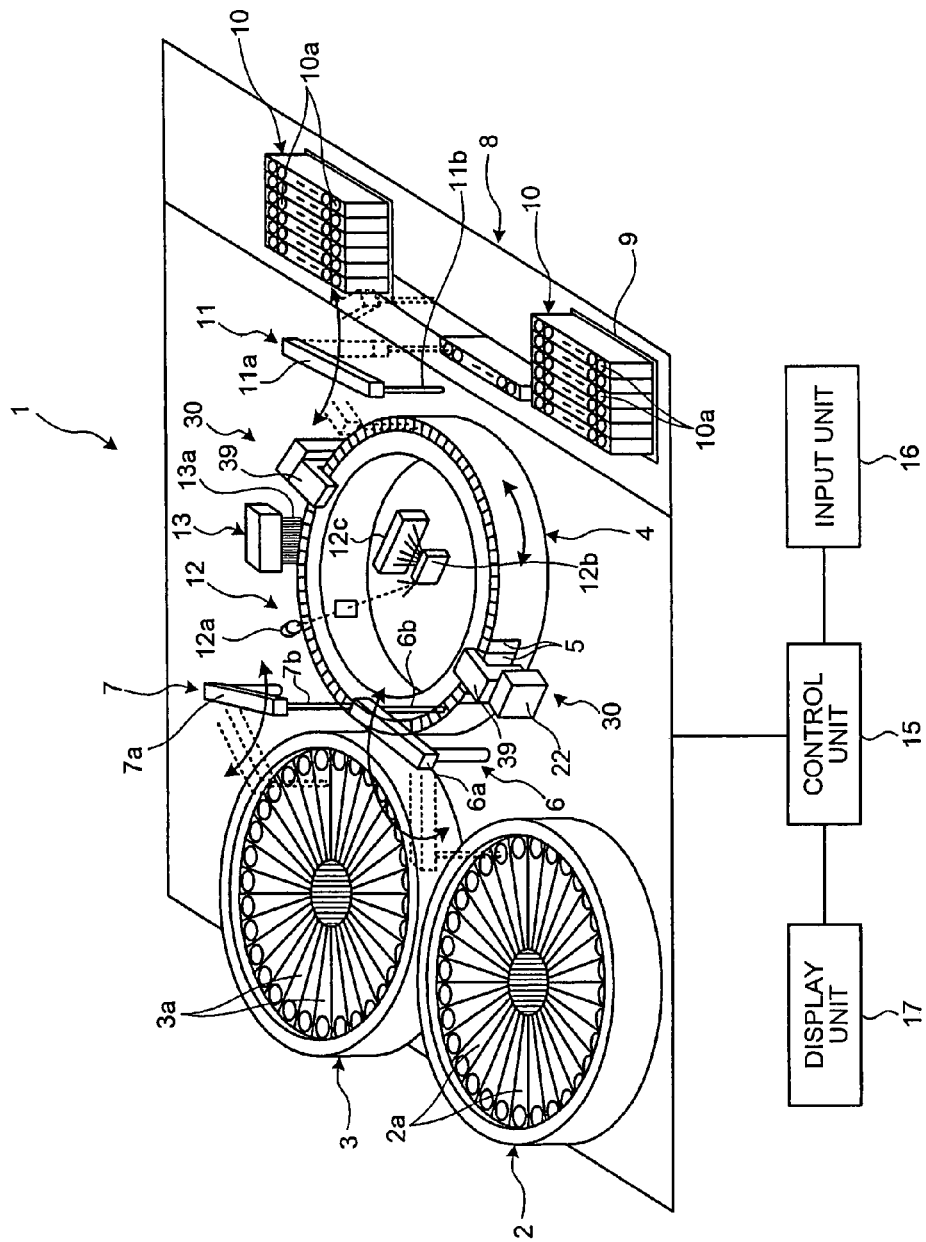
FIG. 20 is a schematic configuration diagram of an automatic analysis apparatus which is employed when the surface-acoustic-wave element is attached to the bottom surface of the vessel.

As described above, when the surface-acoustic-wave element 36 is attached to the bottom surface of the reaction vessel 5, the power transmission element that transmits power to the antenna 36c needs to be arranged at a position vertically opposing to the surface-acoustic-wave element 36. Therefore, in the automatic analysis apparatus 1, a power transmission element 39 supported by the positioning member 22 is formed so as to hang over the reaction vessel 5 on the reaction table 4 as shown in FIG. 20. Further, the power transmission element 39 is provided with an RF transmission antenna (not shown) on a bottom surface portion above the reaction vessel 5. The power transmission element 39 may be formed in such a size that one power transmission element 39 can transmit the power to the plural reaction vessels 5 arranged along the circumferential direction of the reaction table 4, and the RF transmission antenna (not shown) may be formed in a shape corresponding to the plural reaction vessels 5 as shown in FIG. 20. With the above-described configuration, the agitation apparatus 30 can agitate the liquid sample in plural reaction vessels 5 simultaneously.

Figure 21:
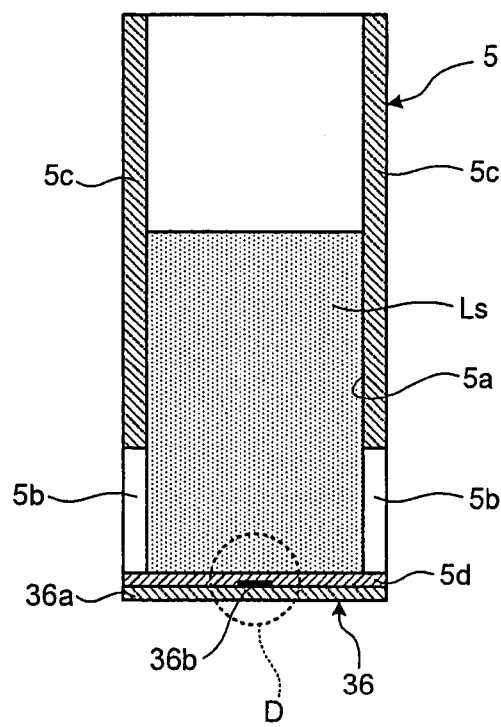
FIG. 21 is a sectional view of a reaction vessel to which the surface-acoustic-wave element is attached in such a manner that the sound wave generator faces a bottom wall.
Figure 22:
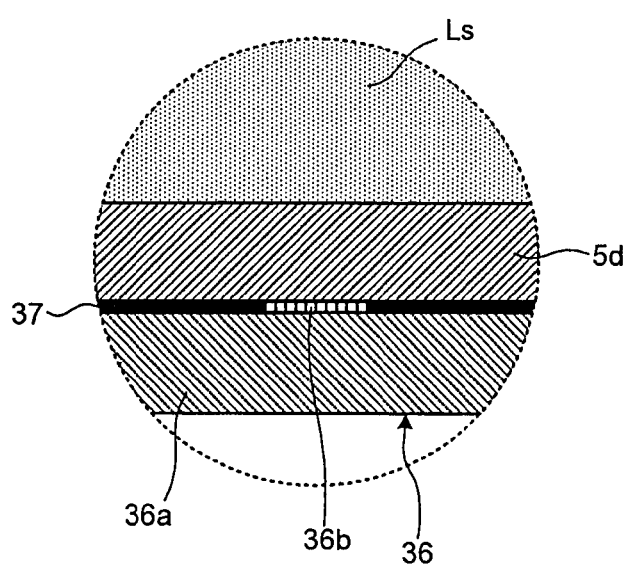
FIG. 22 is an enlarged view of a D-portion of FIG. 21.

When the surface-acoustic-wave element 36 is arranged at the bottom surface of the bottom wall 5d, the surface-acoustic-wave element 36 may be attached to the reaction vessel 5 with the acoustic matching layer 37 placed therebetween while the sound wave generator 36b is kept facing toward the bottom wall 5d, as shown in FIGS. 21 and 22. With such a configuration, the sound wave generator 36b, the antenna (not shown), and the like of the surface-acoustic-wave element 36 are not exposed to the outside and protected by the substrate 36a, and therefore, compared with a configuration in which the sound wave generator 36b, the antenna, and the like are exposed to the outside, a longer-term use of the reaction vessel 5 is allowed.

Figure 23:
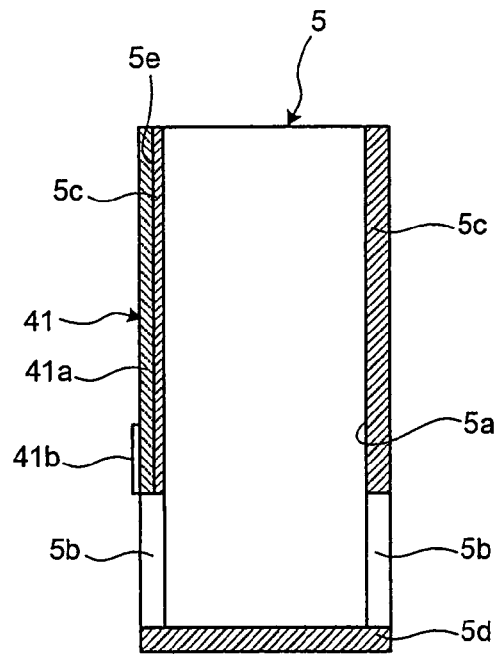
FIG. 23 is a sectional view illustrating another manner of attachment of the surface-acoustic-wave element to the vessel.
Figure 24:
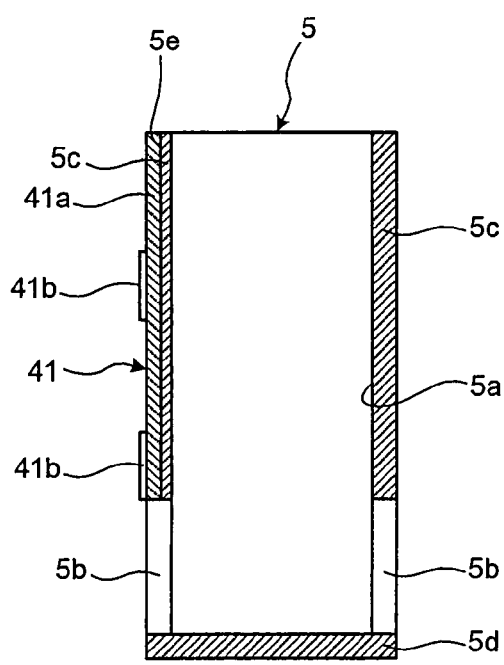
FIG. 24 is a sectional view of a modified example in which two sound wave generators are provided in the surface-acoustic-wave element of FIG. 23.
Figure 25:
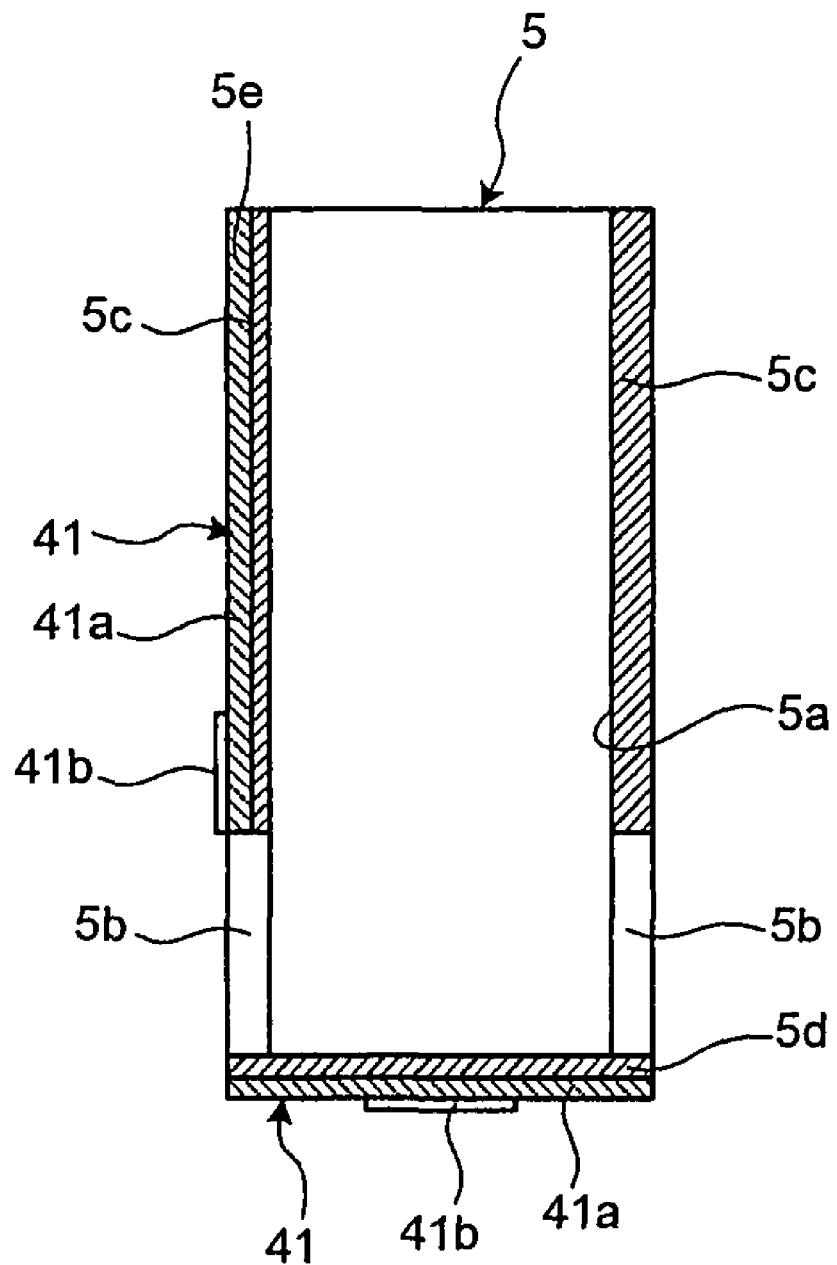
FIG. 25 is a sectional view of a modified example of the vessel in which the surface-acoustic-wave element is arranged on each of a side wall and a bottom surface of the vessel.

Further, since the interdigital transducers (IDT) are employed as the sound wave generator, the surface-acoustic-wave element can be made to have a simplified configuration with a small size. Therefore, in the reaction vessel 5, the antenna of the surface-acoustic-wave element can be arranged at a portion other than the portion where the photometric window 5b is arranged; for example, a depressed portion 5e may be formed as a thinned upper portion of the side wall 5c and the surface-acoustic-wave element 41 may be attached at the depressed portion 5e with the acoustic matching layer (not shown) of epoxy resin or the like posed therebetween as shown in FIG. 23. In a surface-acoustic-wave element 41, a sound wave generator 41b including interdigital transducers (IDT) is formed integrally with the antenna (not shown) that serves as a power receiver on the surface of the substrate 41a. The surface-acoustic-wave element 41 may have two sound wave generators 41b as in the reaction vessel 5 shown in FIGS. 24 and 25. With such a configuration, the agitation capability of the reaction vessel 5 is enhanced, and the liquid sample can be agitated in a short time even when a large volume of liquid sample is retained in the retaining portion 5a.

Figure 26:
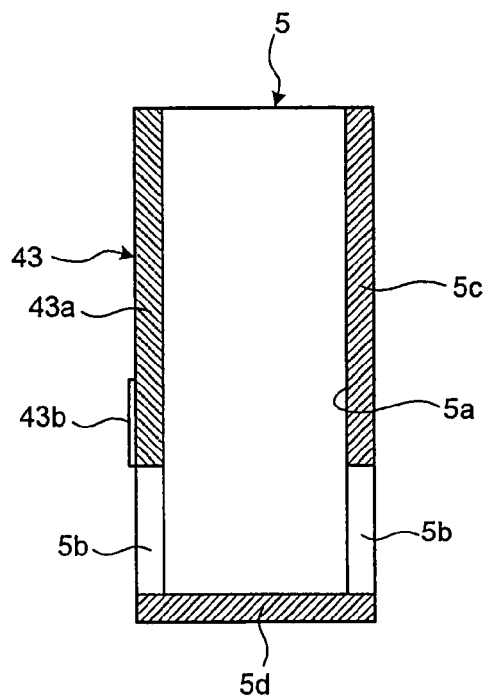
FIG. 26 is a sectional view of an example in which the surface-acoustic-wave element is employed as a part of the side wall of the vessel.
Figure 27:
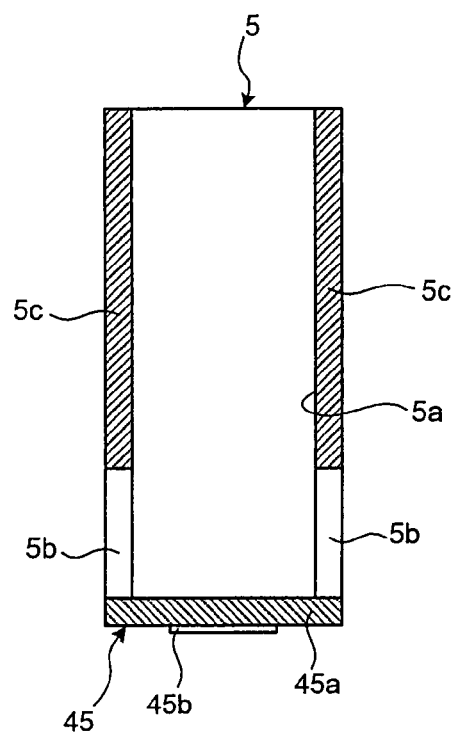
FIG. 27 is a sectional view of an example in which the surface-acoustic-wave element is employed as the bottom wall of the vessel.

Further, since the surface-acoustic-wave element can be formed in a small size, a surface-acoustic-wave element 43 may be employed as a part of the side wall of the reaction vessel 5 as shown in FIG. 26, such that the surface-acoustic-wave element 43 is buried above the window 5b. In the surface-acoustic-wave element 43, a sound wave generator 43b including interdigital transducers (IDT) is formed integrally with the antenna (not shown) serving as a power receiver on the surface of the substrate 43a. Further, the reaction vessel 5 may employ a surface-acoustic-wave element 45 as the bottom wall as shown in FIG. 27. The surface-acoustic-wave element 45 includes a sound wave generator 45b including interdigital transducers (IDT) and an antenna (not shown) serving as a power receiver and formed integrally on the surface of a substrate 45a, and is attached to the reaction vessel 5 while the sound wave generator 45b is kept facing downward.

Figure 11:
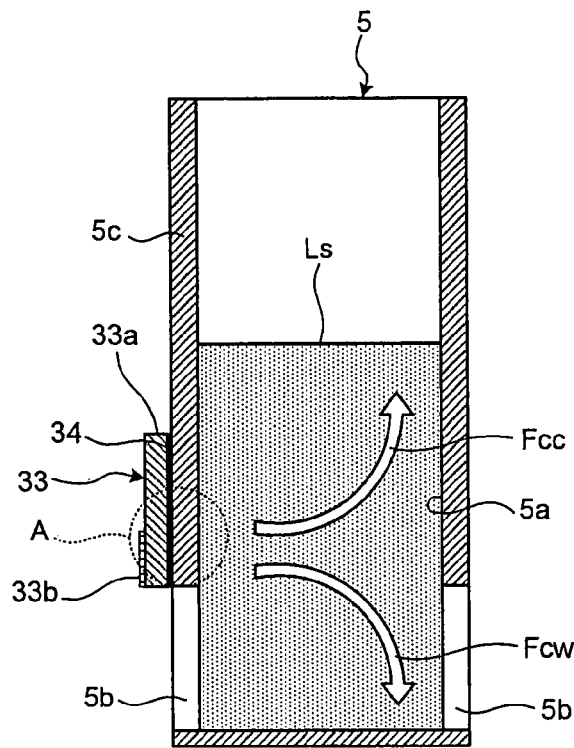
FIG. 11 is a sectional view illustrating flows of a liquid sample along a section of the vessel shown in FIG. 9.
Figure 12:
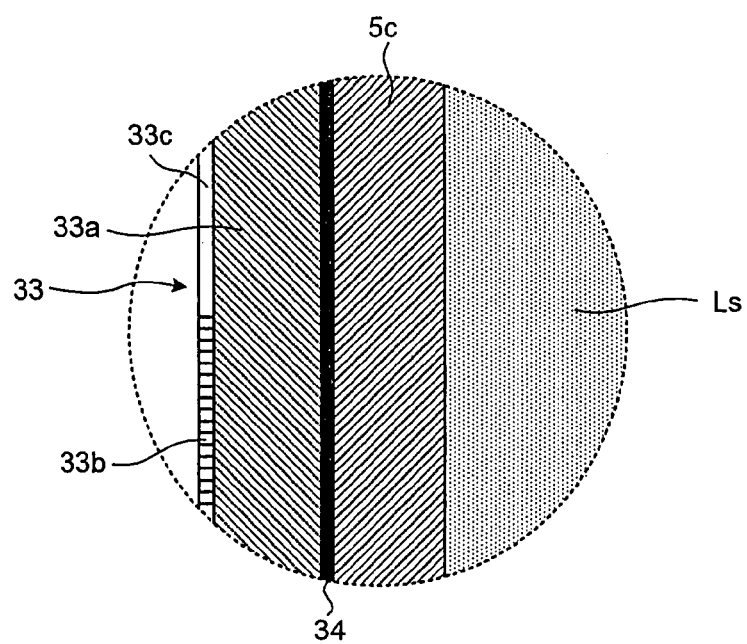
FIG. 12 is an enlarged view of an A-portion of FIG. 11.

In the reaction vessel 5, the counterclockwise flow Fcc and the clockwise flow Fcw are generated by the ultrasound waves generated by the sound wave generator of the surface-acoustic-wave element as shown in FIGS. 11 and 16 and agitate the dispensed reagent and the specimen. However, in the reaction vessel 5 which is a rectangular-tube-like vessel, simple flows that move merely upward and downward take a long time until eventually achieving a uniform agitation of the contents, and contents near the four bottom corners are difficult to agitate.

Figure 28:
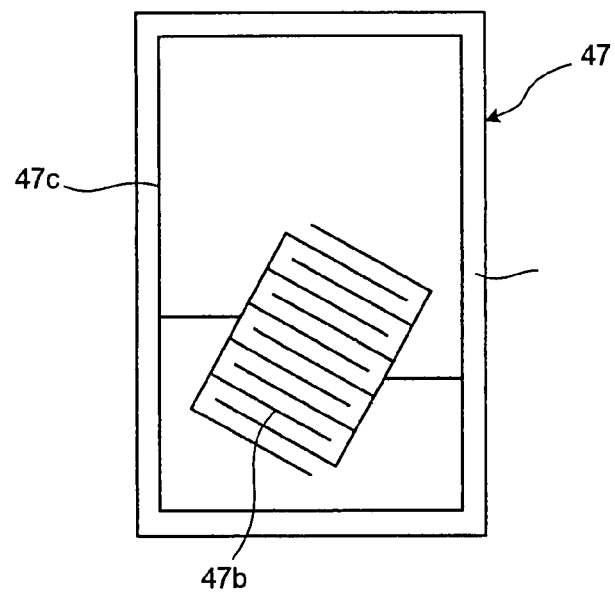
FIG. 28 is a front view of a modified example of the surface-acoustic-wave element.
Figure 29:
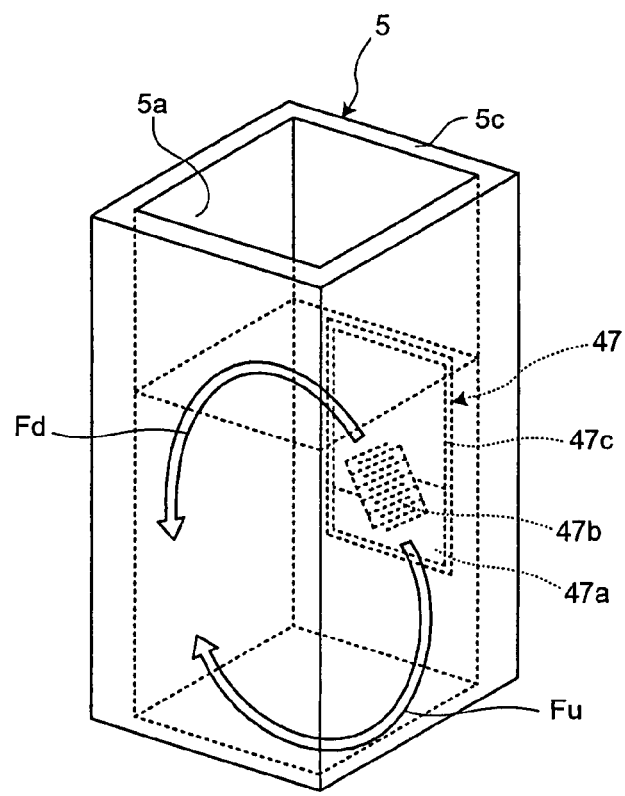
FIG. 29 is a perspective view illustrating flows of a liquid sample in the vessel in which the surface-acoustic-wave element of FIG. 28 is attached to the side wall.

The reaction vessel 5 may include a surface-acoustic-wave element 47 shown in FIG. 28 to alleviate the above problems. As shown in FIG. 28, the surface-acoustic-wave element 47 includes a sound wave generator 47b including plural interdigital transducers (IDT) and an antenna 47c as the power receiver integrally formed on the surface of a substrate 47a, and the entire sound wave generator 47b is arranged in a slanted manner. In other words, the surface-acoustic-wave element 47 is arranged on the side wall 5c of the reaction vessel 5 in such a manner that each interdigital transducer extends along an inclined direction with respect to the horizontal direction and the plural interdigital transducers are arranged in an inclined direction with respect to the vertical direction, as shown in FIG. 29. The surface-acoustic-wave element 47 is attached to the reaction vessel 5 with the acoustic matching layer (not shown) of epoxy resin or the like posed therebetween.

Figure 30:
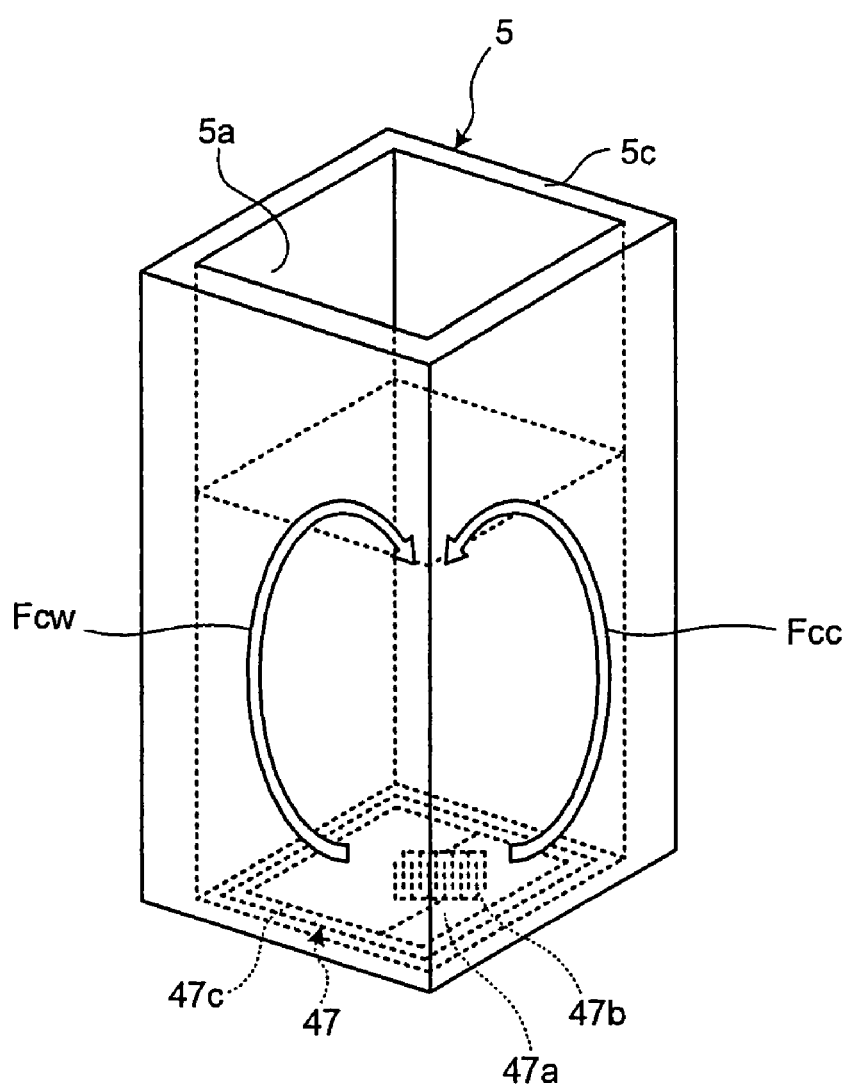
FIG. 30 is a perspective view illustrating flows of a liquid sample in the vessel in which the surface-acoustic-wave element of FIG. 28 is attached to the bottom wall.

Therefore, when the power is transmitted from the power transmission element 31 in a non-contact manner, a flow Fd which moves obliquely upward and is reflected at a liquid surface to return obliquely downward and a flow Fu which moves obliquely downward at a direction forming an angle of 180° with the direction of the flow Fd, is reflected at an inner bottom surface and passes through a corner portion to return in an obliquely upward direction are generated in the liquid sample as shown by arrows of FIG. 29 originating from a position corresponding to the sound wave generator 47b. Two flows Fd and Fu have inclined components with respect to the vertical direction and the directions of flows differ from each other by 180°. Since the two flows Fd and Fu move near the four bottom corners of the reaction vessel 5, the entire liquid sample retained in the retaining portion 5a can be agitated in a short time. When a further surface-acoustic-wave element 47 is provided on the side wall 5c which is opposite to the side wall 5c where the other surface-acoustic-wave element 47 is provided in the reaction vessel 5, two flows Fd and Fu generated respectively by two surface-acoustic-wave elements 47 intersect in the liquid sample to further enhance the agitation efficiency. As shown in FIG. 30, when the surface-acoustic-wave element 47 is arranged on the bottom surface of the reaction vessel 5 such that the arranged direction of the plural interdigital transducers of the sound wave generator 47b is parallel to the diagonal line of the bottom surface, the counterclockwise flow Fcc and the clockwise flow Fcw agitating the contents near the bottom corners of the vessel are generated, whereby the agitation efficiency is enhanced.

Figure 31:
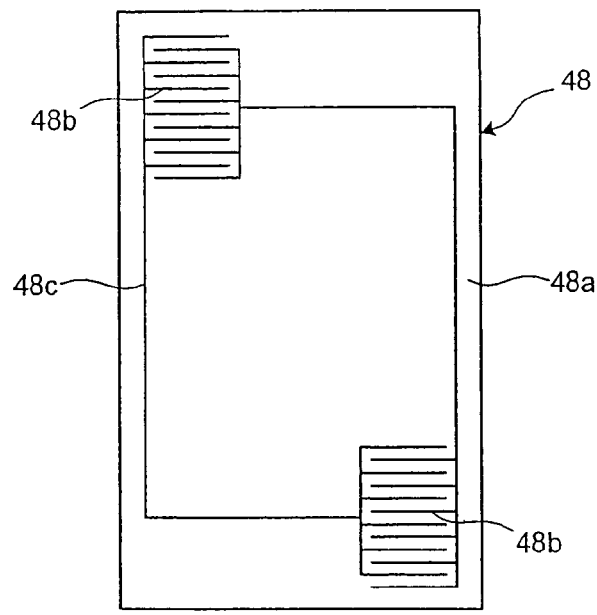
FIG. 31 is a front view of another modified example of the surface-acoustic-wave element.

Further, a surface-acoustic-wave element 48 shown in FIG. 31 may be attached to the bottom surface of the reaction vessel 5. As shown in FIG. 31, the surface-acoustic-wave element 48 includes two sound wave generators 48b including plural interdigital transducers (IDT) and an antenna 48c serving as a power receiver formed integrally on the surface of a substrate 48a, and two sound wave generators 48b are arranged on the diagonal line. The surface-acoustic-wave element 48 is attached to the reaction vessel 5 with the acoustic matching layer (not shown) of epoxy resin or the like posed therebetween.

Figure 32:
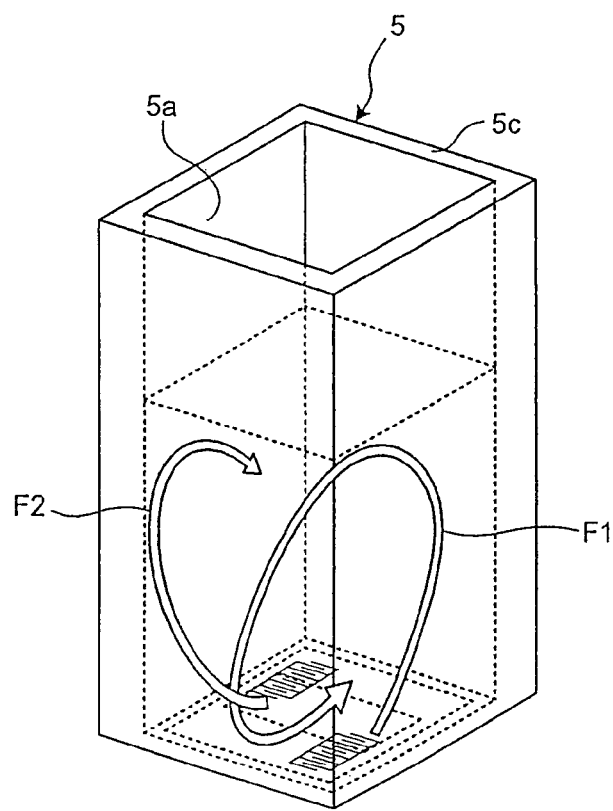
FIG. 32 is a perspective view illustrating flows of a liquid sample in the vessel in which the surface-acoustic-wave element of FIG. 31 is attached to the bottom wall.

When the power is transmitted from the power transmission element 31 in a non-contact manner, since the two sound wave generators 48b are arranged at two corners of the four bottom corners, two flows F1 and F2 are generated as refluxes in the liquid sample in the reaction vessel 5 originating from positions corresponding to the sound wave generators 48b, and reflected at the liquid surface or the side wall 5c as shown by arrows in FIG. 32. Since the two flows F1 and F2 move close to the four bottom corners in the reaction vessel 5, the entire liquid sample can be agitated in a short time.

Third Embodiment

Figure 33:
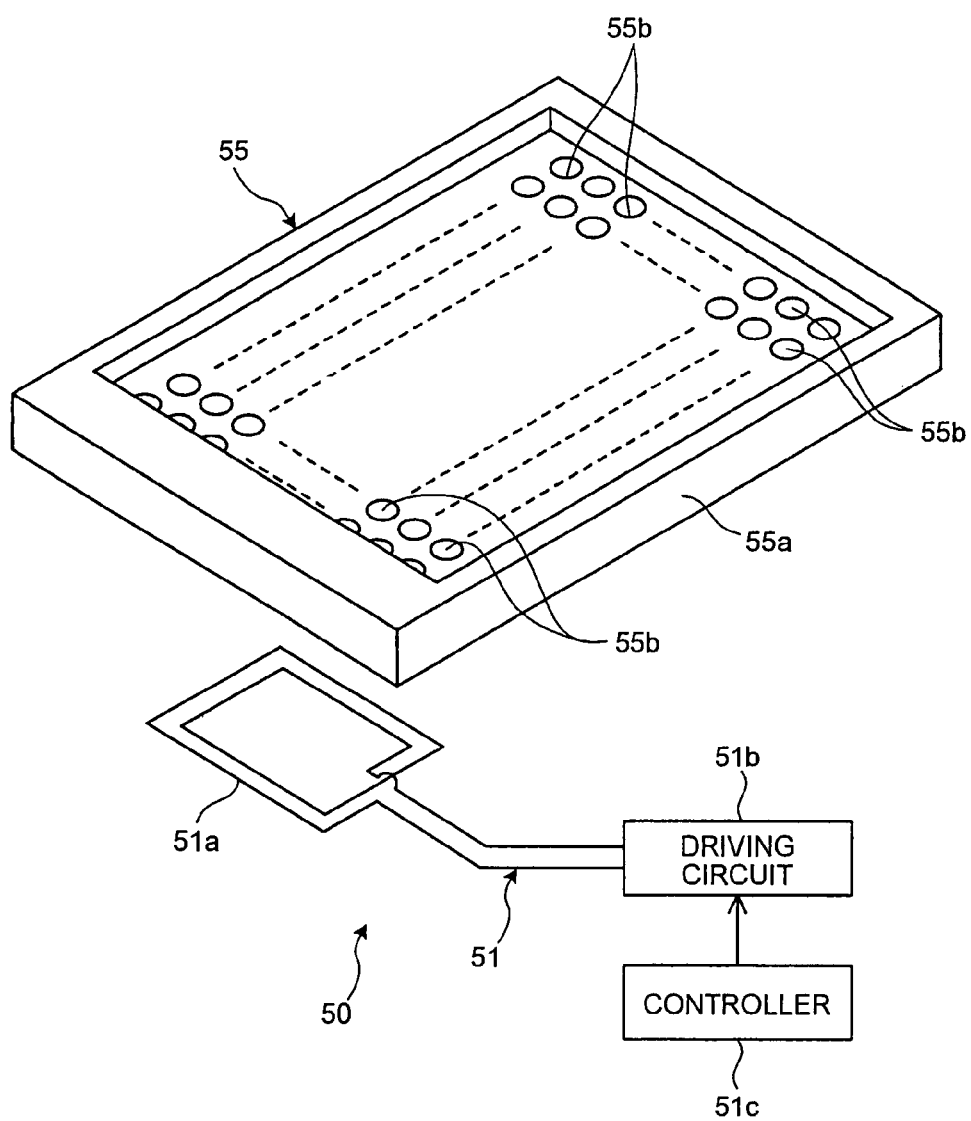
FIG. 33 shows a third embodiment of the present invention, and is a perspective view of an agitation apparatus and a microplate which has plural retaining portions for retaining a liquid according to the third embodiment.
Figure 34:
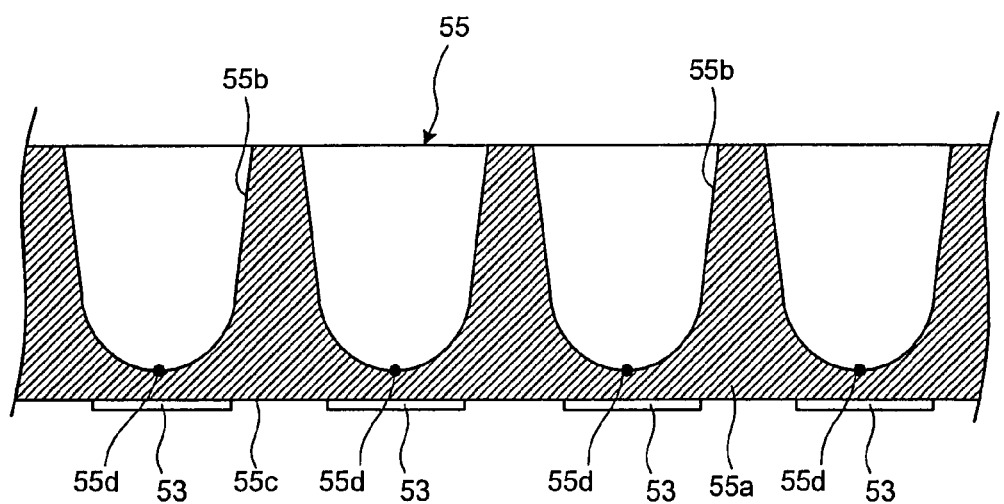
FIG. 34 is a partial sectional view of the microplate of FIG. 33 and the surface-acoustic-wave element.
Figure 35:
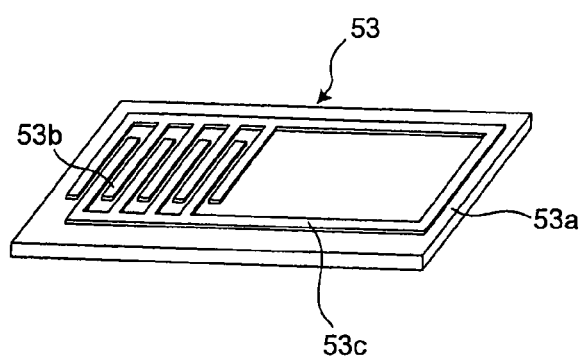
FIG. 35 is an enlarged perspective view of the surface-acoustic-wave element of FIG. 33.

An agitation vessel according to a third embodiment of the present invention will be described in detail with reference to the accompanying drawings. The agitation vessel of the first or the second embodiment has only one liquid retaining portion, whereas the agitation vessel of the third embodiment has plural liquid retaining portions. FIG. 33 is a perspective view of an agitation apparatus and a microplate having plural retaining portions retaining the liquid. FIG. 34 is a partial sectional view of the microplate of FIG. 33 and surface-acoustic-wave elements. FIG. 35 is an enlarged perspective view of the surface-acoustic-wave element of FIG. 33.

A microplate 55 includes, as shown in FIGS. 33 and 34, a main body 55a formed in a rectangular shape, plural wells 55b arranged like a matrix on an upper surface of the main body 55a and serve as retaining portions of the liquid sample, and a surface-acoustic-wave elements 53 serving as a sound wave generator and provided on a bottom surface 55c at respective positions below the wells 55b. The microplate 55 is a reaction vessel employed to receive dispensed reagent and specimen such as blood and bodily fluid in each well 55b to induce reaction and to optically measure the reaction liquid to analyze the component, concentration, or the like of the specimen. The reagent and the specimen dispensed in each well 55b of the microplate 55 are agitated by an agitation apparatus 50. The agitation apparatus 50 has, as shown in FIGS. 33 and 34, a power transmission element 51 and a surface-acoustic-wave element 53.

The power transmission element 51 is supported by a positioning member (not shown) which controls a distance from the microplate 55 and a two-dimensional position along a plate surface of the microplate 55, and includes an RF transmission antenna 51a which is arranged opposite to the plural surface-acoustic-wave element 53, a driving circuit 51b, and a controller 51c as shown in FIG. 33. The power transmission element 51 transmits the power supplied from an alternate-current power supply as electric waves to the surface-acoustic-wave element 53 via the RF transmission antenna 51a while moving in the two-dimensional direction along the plate surface of the microplate 55. The relative arrangement of the power transmission element 51 is determined by the positioning member so that the RF transmission antenna 51a and an antenna 53c described later of the surface-acoustic-wave element 53 are opposed to each other at the time of power transmission to the surface-acoustic-wave element 53.

The surface-acoustic-wave element 53 is a sound wave generating member which is attached to the bottom surface 55c at the bottom portion of each well 55b with an acoustic matching layer (not shown) of epoxy resin or the like posed therebetween. As shown in FIG. 35, a sound wave generator 53b including the interdigital transducers (IDT) and the antenna 53c serving as a power receiver are formed integrally on the surface of the substrate 53a. The surface-acoustic-wave element 53 is positioned so that the center of the sound wave generator 53b is aligned with a vertex 55d of the well 55b and attached to the bottom surface 55c of the microplate 55. One surface-acoustic-wave element 53 may be attached to each well 55b as shown in FIG. 34, or one surface-acoustic-wave element 53 may be attached to a unit of plural wells 55b. The surface-acoustic-wave element 53 receives the electric waves transmitted from the power transmission element 51 by the antenna 53c to generate the surface acoustic waves (ultrasound waves) in the sound wave generator 53b according to the electromotive force generated by the resonance.

In the microplate 55 having the above-described configuration, the power transmission element 51 transmits the electric waves from the RF transmission antenna 51a under the control of the controller 51c when the RF transmission antenna 51a and the antenna 53c oppose with each other in the agitation apparatus 50. The antenna 53c of the surface-acoustic-wave element 53 placed opposite to the power transmission element 51 receives the electric waves, and the electromotive force is generated by the resonance. In the agitation apparatus 50, the surface acoustic waves (ultrasound waves) are generated in the sound wave generator 53b due to the electromotive force, and the surface acoustic waves propagate through the acoustic matching layer to the inside of the main body 55a of the microplate 55, and then leak out to the liquid sample having a close acoustic impedance. As a result, in the microplate 55, the flows are generated in the liquid sample and the reagent and the specimen dispensed in each well 55b are agitated.

After the agitation and the reaction of the reagent and the specimen, an imager such as a CCD camera picks up an image of the liquid sample from above the microplate 55, and the components of the specimen are analyzed based on obtained imaged data.

As described above, the microplate 55 includes plural surface-acoustic-wave elements 53 provided on the bottom surface 55c via the acoustic matching layer not shown in an integral manner, and the power transmission element 51 transmits power to the microplate 55 in a non-contact manner, whereby the reagent and the specimen dispensed in the plural wells 55b are agitated. Since the ultrasound waves generated in the surface-acoustic-wave element 53 propagate through the acoustic matching layer and the bottom surface 55c and are rarely attenuated, the microplate 55 has excellent energy transmission efficiency and a simplified configuration. Therefore, the use of the microplate 55 enhances the energy transmission efficiency in the agitation apparatus 50, and simplifies the configuration further than the agitation apparatus 20 of the first embodiment. Further, since the use of the microplate 55 can eliminate the use of the bath retaining the constant-temperature water as the acoustic matching layer, the automatic analysis apparatus including the agitation apparatus 50 and the agitation apparatus 50 itself can be downsized and the maintenanceability thereof can be improved.

INDUSTRIAL APPLICABILITY

As can be seen from the foregoing, an agitation vessel according to the present invention has excellent transmission efficiency of the energy from the sound wave generator to the agitation vessel, and therefore, the use thereof in an agitation apparatus and an analysis apparatus is useful for enhancing the energy transmission efficiency in the agitation apparatus and the analysis apparatus, simplifying the configuration of the agitation apparatus and the analysis apparatus, and realizing the downsizing and improved maintenanceability, and in particular the agitation vessel of the present invention is suitable for use in an automatic analysis apparatus.

The invention claimed is:
1. An agitation vessel for agitating retained liquid by sound waves, comprising a sound wave generating member and an acoustic matching layer integral with the agitation vessel, the sound wave generating member generating the sound waves that agitate liquid retained in said agitating vessel;
a bottom wall and at least four side walls, wherein a part of the opposing side walls of the at least four side walls is made of an optically transparent material that transmits analytical light to form a photometric window to optically measure the liquid agitated;

wherein the sound wave generating member is attached to an external surface of any of the at least four side walls or the bottom wall and the acoustic matching layer placed between the sound wave generating member and the external surface of any of the at least four side walls or bottom wall; and wherein the sound wave generating member includes on a substrate a sound wave generator having one or a plurality of interdigital transducers of a surface-acoustic-wave element, and a power receiver which receives power and transmits the power to the sound wave generator.

2. The agitation vessel according to claim 1, wherein the bottom wall and at least four side walls are made of an optically transparent material.

3. The agitation vessel according to claim 1, wherein the sound wave generating member is provided on the side wall, on which the photometric window is arranged, among the at least four side walls.

4. The agitation vessel according to claim 3, wherein the sound wave generating member is provided at a portion other than a portion where the photometric window is provided in the side wall.

5. The agitation vessel according to claim 1, wherein the sound wave generating member is provided on the side wall other than the side wall, on which the photometric window is arranged, of the at least four side walls, or on the bottom wall.

6. The agitation vessel according to claim 1, wherein the sound wave generating member is attached to a depressed portion formed on any of the at least four side walls.

7. The agitation vessel according to claim 1, wherein the sound wave generating member constitutes one of the bottom wall and the at least four side walls.

8. The agitation vessel according to claim 1, wherein the at least four side walls retain the liquid on an upper surface of a plate-like member formed of an optically transparent material.

9. The agitation vessel according to claim 1, wherein the sound wave generating member is attached to the side wall or the bottom wall with the sound wave generator and the power receiver facing inward.

10. The agitation vessel according to claim 9, wherein the sound wave generating member is arranged on the bottom wall, and the sound wave generator is arranged so that the one or plurality of interdigital transducers are aligned in a horizontal direction.

11. The agitation vessel according to claim 9, wherein the sound wave generating member is arranged on the side wall, and the sound wave generator is arranged so that each of the one or plurality of 1 interdigital transducers extends horizontally or extends in an inclined direction with respect to a horizontal direction, and the one or plurality of interdigital transducers are arranged along a vertical direction or in an inclined direction with respect to the vertical direction.

12. The agitation vessel according to claim 1, wherein the sound wave generating member is attached to the side wall or the bottom wall with the sound wave generator and the power receiver facing outward.

13. The agitation vessel according to claim 12, wherein the sound wave generating member is arranged on the bottom wall, and the sound wave generator is arranged so that the one or plurality of interdigital transducers are aligned in a horizontal direction.

14. The agitation vessel according to claim 12, wherein the sound wave generating member is arranged on the side wall, and the sound wave generator is arranged so that each of the one or plurality of interdigital transducers extends horizontally or extends in an inclined direction with respect to a horizontal direction, and the one or plurality of interdigital transducers are arranged along a vertical direction or in an inclined direction with respect to the vertical direction.

* * * * *